(12) United States Patent
Hashino et al.

(10) Patent No.: US 9,351,887 B2
(45) Date of Patent: May 31, 2016

(54) ABSORBENT ARTICLE

(71) Applicant: UNICHARM CORPORATION, Shikokuchuo-shi, Ehime (JP)

(72) Inventors: Akira Hashino, Kanonji (JP); Yuki Noda, Kanonji (JP); Tatsuya Tamura, Kanonji (JP); Masashi Nakashita, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 0 days.

(21) Appl. No.: 14/390,001

(22) PCT Filed: Mar. 26, 2013

(86) PCT No.: PCT/JP2013/058860
§ 371 (c)(1),
(2) Date: Oct. 1, 2014

(87) PCT Pub. No.: WO2013/150922
PCT Pub. Date: Oct. 10, 2013

(65) Prior Publication Data
US 2015/0065985 A1 Mar. 5, 2015

(30) Foreign Application Priority Data

Apr. 2, 2012 (JP) .................................. 2012-084294
Sep. 28, 2012 (JP) .................................. 2012-218837

(51) Int. Cl.
*A61F 13/15* (2006.01)
*A61F 13/537* (2006.01)
(Continued)

(52) U.S. Cl.
CPC .............. *A61F 13/537* (2013.01); *A61F 13/513* (2013.01); *A61F 13/51104* (2013.01);
(Continued)

(58) Field of Classification Search
CPC ............ A61F 2013/51059; A61F 2013/51061; A61F 2013/51066; A61F 13/51113; A61F 13/51104; A61F 13/52; A61F 13/511; A61F 13/513
USPC .......................... 604/367, 364, 378, 381, 382
See application file for complete search history.

(56) References Cited

U.S. PATENT DOCUMENTS 3,929,135 A    12/1975  Thompson
4,263,363 A *  4/1981   Buck ....................... A61L 15/20
                                                  428/318.8
(Continued)

FOREIGN PATENT DOCUMENTS

CN    1432352 A    7/2003
EP    1250940 A1   10/2002
(Continued)

OTHER PUBLICATIONS

International Search Report mailed Jul. 2, 2013, corresponds to International Application No. PCT/JP2013/058860.
(Continued)

*Primary Examiner* — Jacqueline Stephens
(74) *Attorney, Agent, or Firm* — Hauptman Ham, LLP

(57) ABSTRACT

The objective of the present disclosure is to provide an absorbent article (1) having a high fiber density region (7) in which absorbed menstrual blood is not easily retained, so that after menstrual blood has been absorbed, feelings of stickiness are not easily caused on a top sheet (2), and the top sheet (2) remains dry. The absorbent article (1) of the present disclosure has a liquid-permeable top sheet (2), a liquid-impermeable back sheet (6), and an absorbent body (3). The absorbent article (1) is characterized by: the top sheet (2) having, in an excretory orifice contact region (A), a high fiber density region (7) and a low fiber density region (8); the top sheet (2) containing, in the excretory orifice contact region (A), a prescribed blood lubricating agent (9); and the basis weight of the blood lubricating agent (9) in the high fiber density region (7) being larger than the basis weight of the blood lubricating agent (9) in the low fiber density region (8).

14 Claims, 5 Drawing Sheets

(51) Int. Cl.
*A61F 13/513* (2006.01)
*A61F 13/538* (2006.01)
*A61L 15/20* (2006.01)
*A61L 15/50* (2006.01)
*A61F 13/51* (2006.01)
*A61F 13/511* (2006.01)

(52) U.S. Cl.
CPC ......... *A61F13/51113* (2013.01); *A61F 13/538* (2013.01); *A61L 15/20* (2013.01); *A61L 15/50* (2013.01); *A61F 13/511* (2013.01); *A61F 13/52* (2013.01); *A61F 2013/51059* (2013.01); *A61F 2013/51061* (2013.01); *A61F 2013/51066* (2013.01)

(56) References Cited

U.S. PATENT DOCUMENTS

| | | |
|---|---|---|
| 4,588,630 A | 5/1986 | Shimalla |
| 4,759,754 A | 7/1988 | Korpman |
| 5,078,710 A | 1/1992 | Suda et al. |
| 5,334,176 A | 8/1994 | Buenger et al. |
| 5,344,416 A | 9/1994 | Niihara |
| 5,614,283 A | 3/1997 | Potnis et al. |
| 5,650,214 A | 7/1997 | Anderson et al. |
| 5,693,037 A * | 12/1997 | Lee ................ A61F 13/512 604/378 |
| 6,153,209 A | 11/2000 | Vega et al. |
| 6,730,819 B1 | 5/2004 | Pesce |
| 2001/0029141 A1 | 10/2001 | Mizutani et al. |
| 2003/0088222 A1 | 5/2003 | Yoshimasa et al. |
| 2003/0149410 A1 | 8/2003 | Kudo et al. |
| 2003/0198784 A1 | 10/2003 | Mizutani et al. |
| 2006/0184150 A1 * | 8/2006 | Noel ................ A61F 13/15203 604/383 |
| 2006/0276767 A1 | 12/2006 | Ueminami et al. |
| 2007/0219515 A1 | 9/2007 | Marsh et al. |
| 2007/0298213 A1 | 12/2007 | Noda et al. |
| 2007/0298214 A1 | 12/2007 | Noda et al. |
| 2007/0298220 A1 | 12/2007 | Noda et al. |
| 2007/0298667 A1 | 12/2007 | Noda et al. |
| 2007/0298671 A1 | 12/2007 | Noda et al. |
| 2007/0299416 A1 | 12/2007 | Noda et al. |
| 2008/0010795 A1 | 1/2008 | Mizutani et al. |
| 2008/0044622 A1 * | 2/2008 | Noda ................ D04H 1/70 428/131 |
| 2008/0044628 A1 | 2/2008 | Noda et al. |
| 2008/0045915 A1 | 2/2008 | Noda et al. |
| 2008/0085399 A1 | 4/2008 | Noda et al. |
| 2008/0132136 A1 | 6/2008 | Uematsu et al. |
| 2008/0147024 A1 | 6/2008 | Potts et al. |
| 2008/0200894 A1 | 8/2008 | Gatto et al. |
| 2009/0221978 A1 | 9/2009 | Gatto et al. |
| 2009/0282660 A1 | 11/2009 | Noda et al. |
| 2010/0069874 A1 | 3/2010 | Noda et al. |
| 2010/0137824 A1 | 6/2010 | Uematsu et al. |
| 2010/0191207 A1 | 7/2010 | Oba et al. |
| 2011/0319851 A1 | 12/2011 | Kudo et al. |
| 2012/0045620 A1 | 2/2012 | Oba et al. |
| 2012/0141742 A1 | 6/2012 | Yamaguchi et al. |
| 2012/0177889 A1 | 7/2012 | Uematsu et al. |
| 2012/0196091 A1 | 8/2012 | Mizutani et al. |
| 2013/0034686 A1 | 2/2013 | Mitsuno |
| 2013/0137328 A1 | 5/2013 | Mitsuno |
| 2013/0226123 A1 | 8/2013 | Kudo et al. |

FOREIGN PATENT DOCUMENTS

| | | |
|---|---|---|
| EP | 1362568 A2 | 11/2003 |
| EP | 1371379 A1 | 12/2003 |
| EP | 2036521 A1 | 3/2009 |
| EP | 2433602 A1 | 3/2012 |
| GB | 2262235 | 6/1993 |
| JP | S57-17081 | 4/1982 |
| JP | S64-34365 | 2/1989 |
| JP | S64-56051 | 3/1989 |
| JP | H01-158954 | 6/1989 |
| JP | 02152920 A | 6/1990 |
| JP | H02-229255 | 9/1990 |
| JP | H05-154176 | 6/1993 |
| JP | H06-5614 U | 1/1994 |
| JP | 6502104 A | 3/1994 |
| JP | H07-84697 | 9/1995 |
| JP | H08-510665 | 11/1996 |
| JP | H08-322879 | 12/1996 |
| JP | H10-95810 | 4/1998 |
| JP | H10-510743 A | 10/1998 |
| JP | H11-512643 | 11/1999 |
| JP | 2000-510376 | 8/2000 |
| JP | 3091283 | 9/2000 |
| JP | 2000-512886 A | 10/2000 |
| JP | 2001-095845 | 4/2001 |
| JP | 2001-129019 | 5/2001 |
| JP | 2001-328191 | 11/2001 |
| JP | 2002-508693 | 3/2002 |
| JP | 3262172 | 3/2002 |
| JP | 2002528174 A | 9/2002 |
| JP | 2002537904 A | 11/2002 |
| JP | 200324372 A | 1/2003 |
| JP | 200352750 A | 2/2003 |
| JP | 2004-500908 | 1/2004 |
| JP | 200449529 A | 2/2004 |
| JP | 2005-504591 A | 2/2005 |
| JP | 2005-095759 | 4/2005 |
| JP | 2005193001 A | 7/2005 |
| JP | 2005-525134 A | 8/2005 |
| JP | 2006501022 A | 1/2006 |
| JP | 2006-510456 | 3/2006 |
| JP | 2006115996 A | 5/2006 |
| JP | 2006-255051 | 9/2006 |
| JP | 2006280526 A | 10/2006 |
| JP | 200714705 A | 1/2007 |
| JP | 2007-509695 A | 4/2007 |
| JP | 2008-002034 A | 1/2008 |
| JP | 2008-023311 A | 2/2008 |
| JP | 2008-025080 | 2/2008 |
| JP | 2008-025081 | 2/2008 |
| JP | 2008-025082 | 2/2008 |
| JP | 2008-025083 | 2/2008 |
| JP | 2008-025084 A | 2/2008 |
| JP | 2008-025085 A | 2/2008 |
| JP | 2008-503323 A | 2/2008 |
| JP | 200823365 A | 2/2008 |
| JP | 200825078 A | 2/2008 |
| JP | 200825079 A | 2/2008 |
| JP | 200829830 A | 2/2008 |
| JP | 2008-138340 A | 6/2008 |
| JP | 2008-144322 A | 6/2008 |
| JP | 2008-529721 A | 8/2008 |
| JP | 2008229032 A | 10/2008 |
| JP | 2008229033 A | 10/2008 |
| JP | 2008237569 A | 10/2008 |
| JP | 2008-264084 A | 11/2008 |
| JP | 2008-266813 A | 11/2008 |
| JP | 2008-541943 A | 11/2008 |
| JP | 2008-307179 | 12/2008 |
| JP | 20095767 A | 1/2009 |
| JP | 2009-030218 A | 2/2009 |
| JP | 2009-201878 | 9/2009 |
| JP | 2009297048 A | 12/2009 |
| JP | 201088822 A | 4/2010 |
| JP | 2010-518918 A | 6/2010 |
| JP | 2010518918 A | 6/2010 |
| JP | 2010-148708 A | 7/2010 |
| JP | 2010526629 A | 8/2010 |
| JP | 2010-285735 | 12/2010 |
| JP | 2010279568 A | 12/2010 |
| JP | 2011-038211 | 2/2011 |
| JP | 2011-074515 A | 4/2011 |
| JP | 2011-080178 | 4/2011 |
| JP | 201167484 A | 4/2011 |
| JP | 201172650 A | 4/2011 |
| JP | 2011510801 A | 4/2011 |

(56) References Cited

FOREIGN PATENT DOCUMENTS

| | | |
|---|---|---|
| JP | 4693847 B2 | 6/2011 |
| JP | 2011104001 A | 6/2011 |
| JP | 2011104059 A | 6/2011 |
| JP | 2011120696 A | 6/2011 |
| JP | 2011226010 A | 11/2011 |
| JP | 2011226011 A | 11/2011 |
| JP | 2012-50626 A | 3/2012 |
| JP | 5122007 B1 | 1/2013 |
| WO | 9301781 A1 | 2/1993 |
| WO | 94/27539 | 12/1994 |
| WO | 96/19173 A1 | 6/1996 |
| WO | 98/55158 A2 | 12/1998 |
| WO | 99/00093 | 1/1999 |
| WO | 99/29274 | 6/1999 |
| WO | 0024351 A1 | 5/2000 |
| WO | 01/45757 | 6/2001 |
| WO | 03/017900 A1 | 3/2003 |
| WO | 03/028776 A1 | 4/2003 |
| WO | 2004030713 A1 | 4/2004 |
| WO | 2004/058119 | 7/2004 |
| WO | 2005/044164 A1 | 5/2005 |
| WO | 2006/009996 A1 | 1/2006 |
| WO | 2006/130646 A1 | 12/2006 |
| WO | 2008072675 A1 | 6/2008 |
| WO | 2008101163 A2 | 8/2008 |
| WO | 2008139425 A1 | 11/2008 |
| WO | 2008/149771 | 12/2008 |
| WO | 2009102837 A2 | 8/2009 |
| WO | 2012/133724 A1 | 10/2012 |

OTHER PUBLICATIONS

International Search Report mailed Jul. 2, 2013, corresponds to International Application No. PCT/JP2013/058862.
International Search Report mailed Jul. 2, 2013, corresponds to International Application No. PCT/JP2013/058861.
International Search Report mailed May 14, 2013, corresponds to International Application No. PCT/JP2013/058836.
International Search Report mailed Mar. 26, 2013, corresponds to International Application No. PCT/JP2012/082977.
International Search Report mailed Jan. 8, 2013, corresponds to International Application No. PCT/JP2012/075583.
International Search Report mailed Jul. 17, 2012, corresponds to International Application No. PCT/JP2012/061505.
Corresponding International Application No. PCT/JP2012/058499 Written Opinion dated Jul. 3, 2012.
Corresponding International Application No. PCT/JP2012/058499 Reply to Written Opinion dated Jan. 30, 2013.
International Search Report mailed May 21, 2013, corresponds to International Application No. PCT/JP2013/058859.
International Search Report mailed Jun. 18, 2013, corresponds to International Application No. PCT/JP2013/058855.
Atsushi Fujita, "Prediction of Organic Compounds and Organic Conceptual Diagram", Kagaku no Ryoiki (Region of Chemistry), Oct. 1957, p. 719-725, vol. 11, No. 10.
International Search Report mailed Jul. 3, 2012 in corresponding International Application No. PCT/JP2012/058499.
International Search Report mailed Mar. 19, 2013 in corresponding International Application No. PCT/JP2012/082087.
International Search Report mailed Mar. 12, 2013 in corresponding International Application No. PCT/JP2012/082104.
International Search Report mailed Mar. 19, 2013 in corresponding International Application No. PCT/JP2013/054382.
International Search Report mailed May 21, 2014 in corresponding International Application No. PCT/JP2013/054796.

* cited by examiner (a)

|—50μm—|

(b)

|—50μm—|

ABSORBENT ARTICLE

CROSS-REFERENCES TO RELATED APPLICATIONS

The present application is a National Phase of International Application Number PCT/JP2013/058860 filed Mar. 26, 2013, which claims the priority of Japanese patent Application No. 2012-084294 filed Apr. 2, 2012 and Japanese patent Application No. 2012-218837 filed Sep. 28, 2012.

TECHNICAL FIELD

The present disclosure relates to an absorbent article.

BACKGROUND ART

As the basic performance of absorbent articles, such as sanitary napkins and panty liners has continued to improve with technological development over many years, leakage after absorption of excreta, such as menstrual blood has become a less frequent occurrence than in the past, and research is currently ongoing with the aim of achieving even higher performance, including a feel similar to underwear, and smoothness of the top sheet even after absorption of excreta, such as menstrual blood.

Menstrual blood during menstruation, in particular, can also contain components of the endometrium which are highly viscous, and the top sheet preferably remains smooth and stick-free even after absorption of such highly viscous menstrual blood. Highly viscous menstrual blood usually remains on the top sheet in the form of masses, generally leaving the user with a visually unpleasant image, and therefore from this viewpoint as well it is preferred for no highly viscous menstrual blood to remain on the top sheet.

For example, PTL 1 discloses an absorbent article having a polypropylene glycol material-containing lotion composition situated on the inner surface of the top sheet (the clothing side surface), the inner surface of the back sheet (the body side surface), and on the base material between the inner surface of the top sheet and the inner surface of the back sheet.

Also, PTL 2 discloses an absorbent article wherein a polypropylene glycol material-containing lotion composition is applied on the outer surface of the top sheet (body side surface).

CITATION LIST

Patent Literature
PTL 1 Japanese Unexamined Patent Publication No. 2010-518918
PTL 2 Japanese Unexamined Patent Publication No. 2011-510801

SUMMARY OF INVENTION

Technical Problem

In a top sheet made of a nonwoven fabric or woven fabric, the absorbed menstrual blood tends to collect by capillary movement in the regions of high fiber density, and the collected menstrual blood often contacts with the skin of the wearer, causing the wearer to feel discomfort. The absorbent articles described in PTLs 1 and 2 are not designed so that absorbed menstrual blood moves into the absorbent body without collecting in the regions of high fiber density.

It is therefore an object of the present disclosure to provide an absorbent article that does not easily retain absorbed menstrual blood in the high fiber density region, and that therefore has reduced stickiness on the top sheet and maintains smoothness on the top sheet, after absorption of menstrual blood.

Solution to Problems

As a result of diligent research directed toward solving the problems described above, the present inventors have discovered an absorbent article comprising a liquid-permeable top sheet, a liquid-impermeable back sheet, and an absorbent body between the top sheet and the back sheet, wherein the top sheet is formed from a nonwoven fabric or woven fabric having in the excretory opening contact region, a high fiber density region, and a low fiber density region with lower fiber density than the high fiber density region, the top sheet comprises in the excretory opening contact region, a blood slipping agent with a kinematic viscosity of 0.01 to 80 $mm^2/s$ at 40° C., a water holding percentage of 0.01 to 4.0 mass % and a weight-average molecular weight of less than 1000, and the basis weight of the blood slipping agent in the high fiber density region is higher than the basis weight of the blood slipping agent in the low fiber density region.

Advantageous Effects of Invention

The absorbent article of the present disclosure does not easily retain absorbed menstrual blood in the high fiber density region, and therefore has reduced stickiness on the top sheet and maintains smoothness on the top sheet, after absorption of menstrual blood.

DESCRIPTION OF EMBODIMENTS

The absorbent article of the present disclosure will now be explained in detail.
[Liquid-Permeable Top Sheet]
In the absorbent article of the present disclosure, the liquid-permeable top sheet is formed from a nonwoven fabric or a woven fabric having, in the excretory opening contact region, a high fiber density region, and a low fiber density region with lower fiber density than the high fiber density region.

There are no particular restrictions on the nonwoven fabric or woven fabric composing the top sheet for the absorbent article of the present disclosure, and for example, it may be a nonwoven fabric having a ridge-furrow structure with a plurality of ridges and a plurality of furrows (hereunder also referred to as "nonwoven fabric with a ridge-furrow structure"), wherein the ridges are high sheet basis weight region with a higher sheet basis weight than the average sheet basis weight of the top sheet, and the furrows are low sheet basis weight region with a lower sheet basis weight than the average sheet basis weight of the top sheet.

A nonwoven fabric with a ridge-furrow structure in which the ridges are high sheet basis weight region and the furrows are low sheet basis weight region may be, for example, (i) a nonwoven fabric in which the ridges are low fiber density regions and the furrows are high fiber density regions, or (ii) a nonwoven fabric in which the ridges are high fiber density regions and the furrows are low fiber density regions.

Examples of (i) nonwoven fabrics in which the ridges are low fiber density regions and the furrows are high fiber density regions include those described in Japanese Unexamined Patent Publication No. 2008-025084, No. 2008-025085, No. 2011-074515 and No. 2009-030218.

Figure 1:
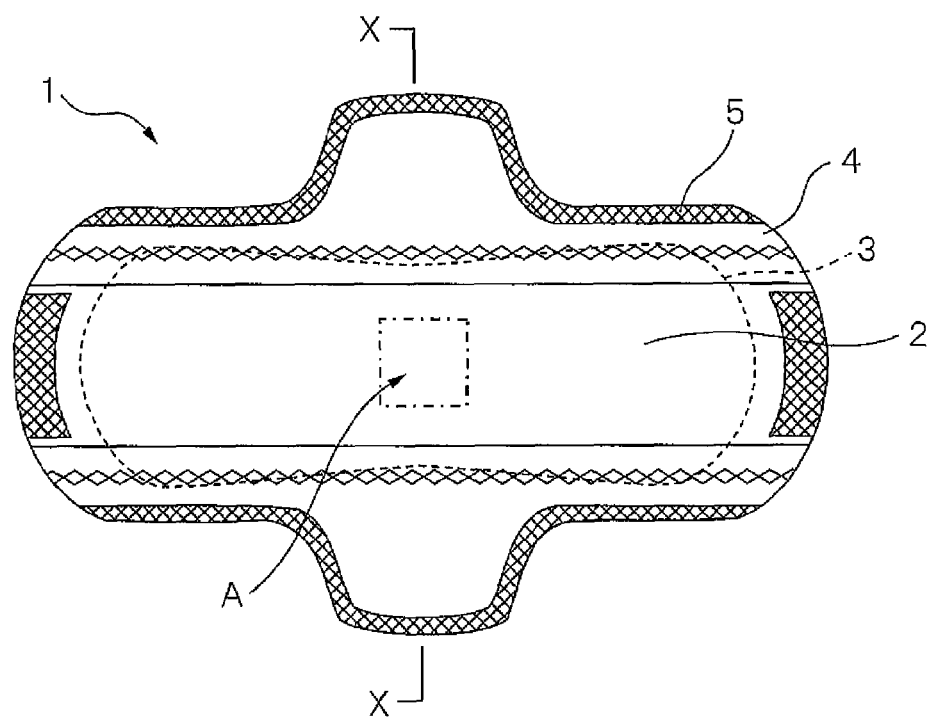
FIG. 1 is a front view of a sanitary napkin according to an embodiment of the absorbent article of the present disclosure.

FIG. 1 is a front view of a sanitary napkin according to an embodiment of the absorbent article of the present disclosure. The sanitary napkin 1 shown in FIG. 1 has its forward direction facing left in the drawing. The sanitary napkin 1 shown in FIG. 1 has a liquid-permeable top sheet 2, an absorbent body 3, and a liquid-impermeable back sheet (not shown). The sanitary napkin 1 in FIG. 1 also has a side sheet 4 and embossed sections 5.

In a different embodiment of the absorbent article of the present disclosure, the absorbent article does not have a side sheet and/or embossed sections. According to yet another embodiment of the absorbent article of the present disclosure, the absorbent article has a second sheet between the top sheet and the absorbent body.

Figure 2:
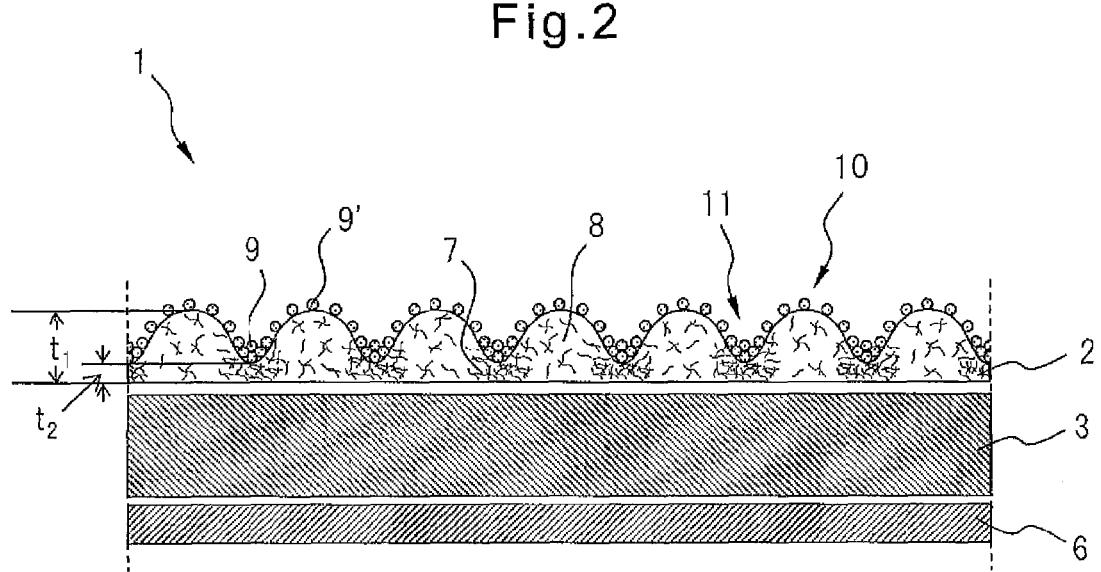
FIG. 2 is a cross-sectional view of section A of the sanitary napkin 1 shown in FIG. 1, along X-X.

FIG. 2 is a cross-sectional view of section A of the sanitary napkin 1 shown in FIG. 1, along X-X. The sanitary napkin 1 shown in FIG. 2 has a liquid-permeable top sheet 2, an absorbent body 3, and a liquid-impermeable back sheet 6. In FIG. 2, the top sheet 2 has a ridge-furrow structure with a plurality of ridges 10 and a plurality of furrows 11, where the ridges 10 are low fiber density regions 8 and the furrows 11 are high fiber density regions 7. Also, in the sanitary napkin 1 shown in FIG. 2, the basis weight of the blood slipping agent 9 in the high fiber density regions 7 is greater than the basis weight of the blood slipping agent 9' in the low fiber density regions 8.

In FIG. 2, the droplet-like blood slipping agents 9 and 9' are shown as being on the skin contact surface of the top sheet 2, but according to the absorbent article of the present disclosure, the form and distribution of the blood slipping agent is not limited to that shown in FIG. 2, and for example, a droplet-like blood slipping agent may be present inside the top sheet.

In the absorbent article of the present disclosure, the high fiber density region has a fiber density of preferably about 0.001 to 0.1 g/cm$^3$ higher and even more preferably about 0.005 to 0.05 g/cm$^3$ higher than the low fiber density region. If the difference in the fiber densities is less than about 0.001 g/cm$^3$, absorbed menstrual blood will not easily be retained in the high fiber density region, and the effect of the blood slipping agent will tend to be lower. If the difference in fiber densities is greater than about 0.1 g/cm$^3$, either the fiber density of the high fiber density region will be higher and the feel of the top sheet on the skin will be impaired, or the fiber density of the low fiber density region will be lower and the top sheet will be more prone to tearing.

Also, the density in the high fiber density region is preferably about 0.005 to about 0.2 g/cm$^3$, and more preferably about 0.007 to 0.07 g/cm$^3$. If the density in the high fiber density region is below 0.005 g/cm$^3$, absorbed menstrual blood will not easily be retained in the high fiber density region, and the effect of the blood slipping agent will tend to be lower, while if the density in the high fiber density region is above 0.07 g/cm$^3$, the fiber density in the high fiber density region will be high, tending to reduce the feel of the top sheet on the skin.

As used herein, the fiber density of the top sheet is determined by dividing the basis weight of the high fiber density region or low fiber density region by its height.

The height is measured using a high precision laser displacement meter, such as an LJ-G Series two-dimensional laser displacement gauge (Model: LJ-G030) by Keyence Corp.

In the absorbent article of the present disclosure, the amount of blood slipping agent in the high fiber density region is greater than the amount of blood slipping agent in the low fiber density region, and the basis weight of the blood slipping agent in the high fiber density region is preferably about 3 to about 90%, more preferably about 5 to about 85% and even more preferably about 10 to about 80% greater than the basis weight of the blood slipping agent in the low fiber density region. If the difference in basis weights is less than about 3%, menstrual blood that has reached the high fiber density region will not be able to rapidly migrate into the absorbent body, and menstrual blood may be retained in the top sheet. If the difference in basis weights is greater than about 90%, either the amount of blood slipping agent in the high fiber density region will be greater, increasing the feeling of wetness during wear, or the amount of blood slipping agent in the low fiber density region will be lower, making it difficult for the blood slipping agent to act on menstrual blood that has reached the low fiber density region.

The basis weight of the blood slipping agent in the high fiber density region is preferably about 1 to about 30 g/m$^2$, more preferably about 2 to about 20 g/m$^2$ and even more preferably about 3 to about 10 g/m$^2$. If the basis weight is less than about 1 g/m$^2$, it may not be possible for menstrual blood that has reached the high fiber density region to rapidly migrate into the absorbent body, while if the basis weight is greater than about 30 g/m$^2$, the feeling of wetness during wear will tend to be increased.

As used herein, the basis weight of the blood slipping agent in the top sheet is measured in the following manner.

(1) The region of the top sheet that is to be measured is cut out using a sharp blade, such as a cutter replacement blade, while minimizing any alteration in thickness, to obtain a sample.

(2) The area of the sample: SA (m$^2$) and the mass: $SM_0$ (g) are measured.

(3) The sample is stirred for at least 3 minutes in a solvent that dissolves the blood slipping agent, such as ethanol or acetone, to dissolve the blood slipping agent in the solvent.

(4) The sample is filtered on weight-measured filter paper, and the sample is thoroughly rinsed with the solvent on the filter paper. The sample on the filter paper is dried in an oven at 60° C.

(5) The masses of the filter paper and sample are measured, and the mass of the filter paper is subtracted to calculate the dry sample mass: $SM_1$ (g).

(6) The basis weight BBS (g/m²) of the blood slipping agent is calculated by the following formula.

$$BBS\,(g/m^2)=[SM_0\,(g)-SM_1\,(g)]/SA\,(m^2)$$

In order to minimize error, multiple samples are taken from multiple absorbent articles, without the total area of the sample exceeding 100 cm², conducting several repeated measurements and taking the average value.

The basis weight of the blood slipping agent in the high fiber density region and the basis weight of the blood slipping agent in the low fiber density region may be measured, for example, by cutting out a sample to be measured, measuring the flat area and weight, and then dipping it in a solvent to dissolve the blood slipping agent, and determining the amount of the separated blood slipping agent from the mass of the dipped sample. The solvent may be, for example, a ketone solvent, such as acetone, an alcohol solvent, such as ethanol, or an aromatic solvent, such as toluene.

The function of the absorbent article of the present disclosure will now be explained with reference to FIG. 2.

Highly viscous menstrual blood that has reached the skin contact surface of the top sheet 2 passes through the top sheet 2 and is absorbed into the absorbent body 3, but the menstrual blood tends to be retained in the high fiber density region 7 by capillary movement as it passes through the top sheet 2. Particularly in the case of a nonwoven fabric with a ridge-furrow structure, such as shown in FIG. 2, menstrual blood that has reached the ridges 10 tends to migrate into the furrows 11, and therefore the menstrual blood is easily retained in the high fiber density region 7 of the furrows 11.

In the absorbent article shown in FIG. 2, since the basis weight of the blood slipping agent 9 in the high fiber density region 7 is higher than the basis weight of the blood slipping agent 9' in the low fiber density region 8, menstrual blood is not easily retained in the high fiber density region 7, and menstrual blood that has reached the high fiber density region 7 rapidly migrates into the interior of the absorbent article together with the blood slipping agent 9, and is absorbed into the absorbent body 3.

Since the blood slipping agent has a kinematic viscosity of about 0.01 to about 80 mm²/s at 40° C., it has very low viscosity near the body temperature of the wearer, and since it has a water holding percentage of about 0.01 to about 4.0 mass %, it exhibits constant affinity with menstrual blood and migrates together with menstrual blood into the absorbent body.

In addition, if the blood slipping agent has a hydrophobic portion composed of a hydrocarbon portion, and a hydrophilic portion composed of a hydrophilic group (a polar group, such as carbonyl, oxy, carboxyl or hydroxyl), a hydrophilic bond (a polar bond, such as a carbonyl bond, ester bond, carbonate bond or ether bond) or the like, the blood slipping agent will have an effect of facilitating sliding of menstrual blood.

The hydrophobic portion of the blood slipping agent repels the hydrophilic components in menstrual blood (such as blood plasma) while the hydrophilic portion of the blood slipping agent attracts the hydrophilic components in menstrual blood (such as blood plasma), and therefore menstrual blood will easily slide into the absorbent body.

In addition, since the blood slipping agent has a water holding percentage of about 0.01 to about 4.0 mass % and its affinity with the hydrophilic components (such as blood plasma) in menstrual blood is not excessively high, less of the menstrual blood remains on the top sheet.

For an embodiment in which the nonwoven fabric composing the top sheet is a nonwoven fabric with a ridge-furrow structure having a plurality of ridges and a plurality of furrows, the top parts of the ridges are preferably about 0.1 to about 15.0 mm higher, more preferably about 0.5 to about 5.0 mm higher and even more preferably about 0.5 to about 2.0 mm higher than the bottom parts of the furrows. The pitch of the ridges is preferably about 1.5 to about 17 mm, more preferably about 2.0 to about 12 mm and even more preferably about 3 to about 8 mm. This is to allow menstrual blood to slide down from the ridges into the furrows, and then to utilize the sliding energy so that the menstrual blood passes into the furrows (high fiber density region) and rapidly migrate into the absorbent body.

The heights of the top parts of the ridges and the bottom parts of the furrows are the heights from the bottom parts of the top sheet 2, represented in FIG. 2 by $t_1$ and $t_2$, respectively.

As used herein, the term "ridge" refers to a section having a height that is at least halfway between the heights of the top parts of the ridges and the heights of the bottom parts of the furrows, while the term "furrow" refers to a section having a height that is less than halfway between the heights of the top parts of the ridges and the heights of the bottom parts of the furrows.

For example, in FIG. 2, the ridges are the sections where the height is at least $(t_1+t_2)/2$ and no greater than $t_1$, and the furrows are the sections were the height is at least $t_2$ and less than $(t_1+t_2)/2$.

Figure 3:
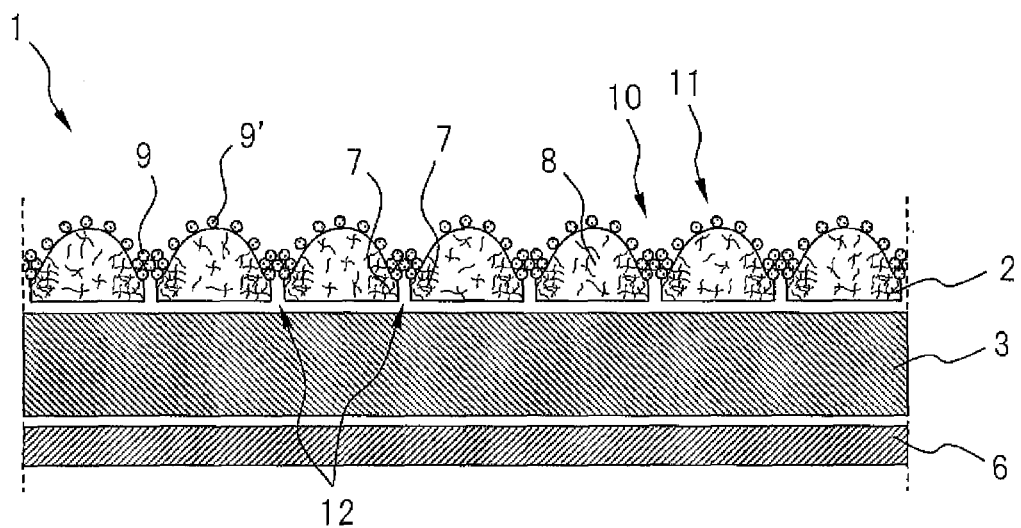
FIG. 3 is a cross-sectional view of a sanitary napkin according to another embodiment of the absorbent article of the present disclosure.

FIG. 3 is a cross-sectional view of a sanitary napkin, according to another embodiment of the absorbent article of the present disclosure. FIG. 3 is a cross-sectional view corresponding to cross-section X-X at section A of the sanitary napkin 1 shown in FIG. 1. The absorbent article shown in FIG. 3 is generally identical to the one shown in FIG. 2, but the sanitary napkin 1 in FIG. 3 has open holes 12 in the furrows 11.

The top sheet 2 shown in FIG. 3 can be produced, for example, according to Japanese Unexamined Patent Publication No. 2008-25084 or Japanese Unexamined Patent Publication No. 2008-25085.

In an embodiment wherein the top sheet is a nonwoven fabric with a ridge-furrow structure and open holes are present in the furrows, as illustrated in FIG. 3, menstrual blood that tends to be retained in the high fiber density region 7 by capillary movement rapidly migrates into the absorbent article and be absorbed into the absorbent body 3, together with the blood slipping agent 9 present in the high fiber density region 7. In the embodiment wherein the top sheet is a nonwoven fabric with a ridge-furrow structure and open holes are present in the furrows, as illustrated in FIG. 3, menstrual blood is caused to slide down from the ridges 10 (low fiber density region 8) into the furrows 11 (high fiber density region 7), and that energy is then utilized to cause the menstrual blood to pass through the open holes 12 and rapidly migrate into the absorbent body 3.

Examples of (ii) nonwoven fabrics in which the ridges are high fiber density region and the furrows are low fiber density region include those described in Japanese Unexamined Patent Publication No. 2008-002034 and No. 2008-023311.

Figure 4:
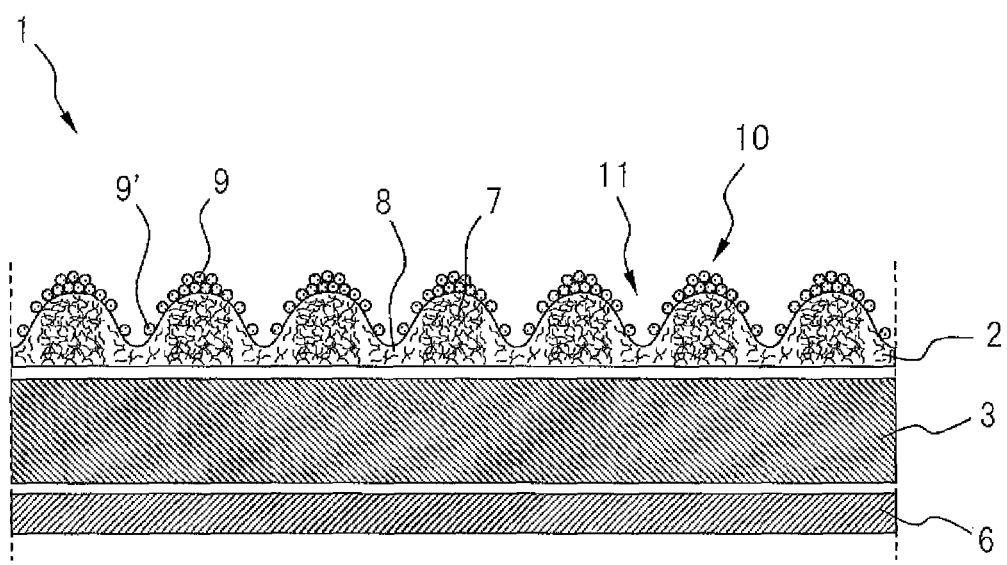
FIG. 4 is a cross-sectional view of a sanitary napkin according to another embodiment of the absorbent article of the present disclosure.

FIG. 4 is a cross-sectional view of a sanitary napkin, according to another embodiment of the absorbent article of the present disclosure. FIG. 4 is a cross-sectional view corresponding to cross-section X-X at section A of the sanitary napkin 1 shown in FIG. 1. The sanitary napkin 1 shown in FIG. 4 has a liquid-permeable top sheet 2, an absorbent body 3, and a liquid-impermeable back sheet 6. In FIG. 4, the top sheet 2 has a ridge-furrow structure with a plurality of ridges 10 and a plurality of furrows 11, where the ridges 10 are high fiber density region 7 and the furrows 11 are low fiber density region 8. Also, in the sanitary napkin 1 shown in FIG. 4, the basis weight of the blood slipping agent 9 in the high fiber density region 7 is greater than the basis weight of the blood slipping agent 9' in the low fiber density region 8.

A top sheet which is a nonwoven fabric with a ridge-furrow structure, wherein the ridges are high fiber density region and the furrows are low fiber density region, is advantageous in that it is resistant to collapse of the ridge-furrow structure, and air permeability in the planar direction is excellent, but menstrual blood is also retained in the ridges which are the high-density fiber regions, tending to produce an uncomfortable feel for the wearer. However, by including a blood slipping agent with a greater basis weight in the ridges, which are the high fiber density region, than in the furrows, which are the low fiber density region, as shown in FIG. 4, menstrual blood is retained less easily in the ridges and the menstrual blood easily migrates into the absorbent article.

Incidentally, in an absorbent article, such as illustrated in FIG. 4, menstrual blood does not only migrate through the interior of the ridges but also slides along the surface (skin contact surface) of the ridges into the furrows, and then migrates from the furrows into the absorbent body.

Figure 5:
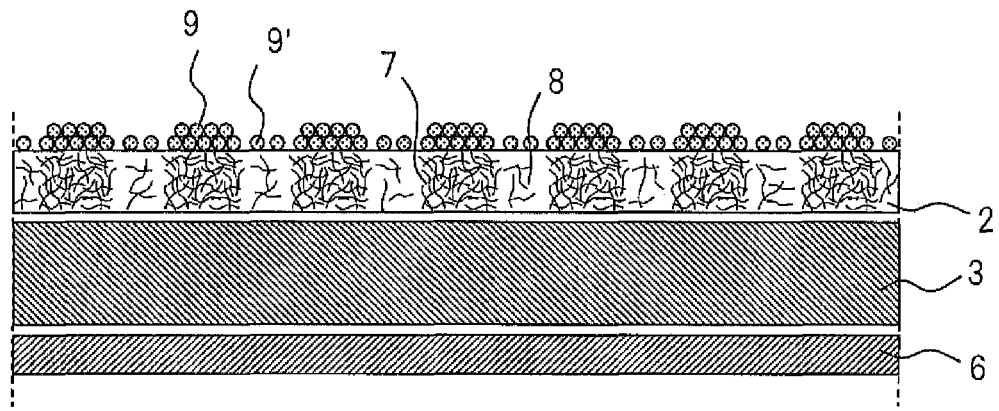
FIG. 5 is a cross-sectional view of a sanitary napkin according to another embodiment of the absorbent article of the present disclosure.

FIG. 5 is a cross-sectional view of a sanitary napkin, according to yet another embodiment of the absorbent article of the present disclosure. FIG. 5 is a cross-sectional view corresponding to cross-section X-X at section A of the sanitary napkin 1 shown in FIG. 1. The sanitary napkin 1 shown in FIG. 5 has a liquid-permeable top sheet 2, an absorbent body 3, and a liquid-impermeable back sheet 6. In FIG. 5, the top sheet 2 has high fiber density region 7 and low fiber density region 8. Also, in the sanitary napkin 1 shown in FIG. 5, the basis weight of the blood slipping agent 9 in the high fiber density region 7 is greater than the basis weight of the blood slipping agent 9' in the low fiber density region 8.

The top sheet 2 shown in FIG. 5 can be produced, for example, according to Japanese Unexamined Patent Publication No. 2008-138340, Japanese Unexamined Patent Publication No. 2008-144322, Japanese Unexamined Patent Publication No. 2008-264084 or Japanese Unexamined Patent Publication No. 2008-266813.

In a top sheet which is a nonwoven fabric having low fiber density region and high fiber density region, menstrual blood that has reached the skin contact surface of the top sheet is easily drawn into the high fiber density region by capillary movement, and menstrual blood is easily retained in the high fiber density region. However, if the amount of blood slipping agent 9 in the high fiber density region 7 is greater than the amount of blood slipping agent 9' in the low fiber density region 8, as shown in FIG. 5, the blood slipping agent 9 in the high fiber density region 7 will rapidly migrate into the interior of the absorbent article together with the menstrual blood, and will be absorbed into the absorbent body 3.

[Blood Slipping Agent]

In the absorbent article of the present disclosure, the liquid-permeable top sheet contains, in the excretory opening contact region, a blood slipping agent having a kinematic viscosity of about 0.01 to about 80 $mm^2/s$ at 40° C., a water holding percentage of about 0.05 to about 4.0 mass %, and a weight-average molecular weight of less than about 1000.

The term "excretory opening contact region" as used herein refers to the region bordering the excretory opening of the wearer, and the term "excretory opening" refers to the region including at least the labia minora, and may further include a portion of the labia majora.

According to another embodiment of the absorbent article of the present disclosure, the liquid-permeable top sheet contains the blood slipping agent in a region other than the excretory opening contact region.

The blood slipping agent has, at 40° C., a kinematic viscosity of about 0 to about 80 $mm^2/s$, preferably a kinematic viscosity of about 1 to about 70 $mm^2/s$, more preferably a kinematic viscosity of about 3 to about 60 $mm^2/s$, even more preferably a kinematic viscosity of about 5 to about 50 $mm^2/s$, and yet more preferably a kinematic viscosity of about 7 to about 45 $mm^2/s$.

The kinematic viscosity tends to be higher with a) a larger molecular weight of the blood slipping agent, b) a higher percentage of polar bonds, such as carbonyl bonds (—CO—), ester bonds (—COO—), carbonate bonds (—OCOO—) and ether bonds (—O—), in groups, such as carbonyl groups (—CO—), oxy groups (—O—), carboxyl groups (—COOH), hydroxyl groups (—OH) and the like, and c) a larger IOB, explained below.

In order to have a kinematic viscosity of about 0 to about 80 $mm^2/s$ at 40° C., the melting point of the blood slipping agent is preferably 45° C. or less. This is because the kinematic viscosity will tend to be higher if the blood slipping agent contains crystals at 40° C.

As used herein, the "kinematic viscosity at 40° C." may be referred to simply as "kinematic viscosity".

A kinematic viscosity exceeding about 80 $mm^2/s$ will tend to result in high viscosity of the blood slipping agent, such that it will not as easily migrate into the absorbent body together with menstrual blood that has reached the skin contact surface of the top sheet.

As used herein, the kinematic viscosity is measured according to JIS K 2283:2000, "5. Kinematic Viscosity Test Method", using a Cannon-Fenske reverse-flow viscometer, at a testing temperature of 40° C.

The blood slipping agent has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

As used herein, "water holding percentage" means the percentage of water that is held by a substance, and it is measured in the following manner.

(1) A test tube, a rubber stopper, the substance to be measured and deionized water are allowed to stand for a day and a night in a thermostatic chamber at 40° C.

(2) Into the 20 mL test tube in the thermostatic chamber there are charged 5.0 g of the substance to be measured and 5.0 g of deionized water.

(3) The mouth of the test tube is sealed with the rubber stopper in the thermostatic chamber, and it is rotated once and allowed to stand for 5 minutes.

(4) A 3.0 g portion of the layer of the substance to be measured (usually the upper layer) is sampled into a glass dish with a diameter of 90 mm (mass: $W_0$ (g)), in the thermostatic chamber.

(5) The dish is heated at 105° C. for 3 hours in an oven to evaporate off the moisture, and the mass of each dish is measured (mass: $W_1$ (g)).

(6) The water holding percentage is calculated by the following formula.

Water holding percentage (mass %)=100×[$W_0$ (g)−$W_1$ (g)]/3.0 (g)

The measurement is conducted three times, and the average value is recorded.

A low water holding percentage value will tend to lower the affinity between the blood slipping agent and menstrual blood, thus impeding its migration together with menstrual blood that has reached the skin contact surface of the top sheet. If the water holding percentage value increases, on the other hand, the affinity between menstrual blood and the blood modifying agent will become very high, similar to a surfactant, and absorbed menstrual blood will tend to remain on the skin contact surface of the top sheet, resulting in more red coloration of the skin contact surface of the top sheet.

The water holding percentage value tends to be greater with a) a smaller molecular weight of the blood slipping agent, and b) a higher percentage of polar bonds, such as carbonyl bonds (—CO—), ester bonds (—COO—), carbonate bonds (—OCOO—) and ether bonds (—O—), in groups, such as carbonyl groups (—CO—), oxy groups (—O—), carboxyl groups (—COOH), hydroxyl groups (—OH) and the like. This is because the blood slipping agent has greater hydrophilicity. The water holding percentage will tend to have a larger value with a greater IOB, i.e. with a higher inorganic value or with a lower organic value. This is because the blood slipping agent will have greater hydrophilicity.

The blood slipping agent has a weight-average molecular weight of less than about 1,000, and preferably a weight-average molecular weight of less than about 900. This is because, if the weight-average molecular weight is about 1,000 or higher, tack may result in the blood slipping agent itself, tending to create a feeling of unpleasantness for the wearer. If the weight-average molecular weight increases, the viscosity of the blood slipping agent will tend to increase, and it will therefore be difficult to lower the viscosity of the blood slipping agent by heating to a viscosity suitable for coating, and as a result, the blood slipping agent may need to be diluted with a solvent.

The blood slipping agent preferably has a weight-average molecular weight of about 100 or greater, and more preferably it has a weight-average molecular weight of about 200 or greater. This is because if the weight-average molecular weight is low, the vapor pressure of the blood slipping agent may be increased, gasification may occur during storage and the amount may be reduced, often leading to problems, such as odor of the blood slipping agent during wear.

In addition, as used herein, "weight-average molecular weight" includes the concept of a polydisperse compound (for example, a compound produced by stepwise polymerization, an ester formed from a plurality of fatty acids and a plurality of aliphatic monohydric alcohols), and a simple compound (for example, an ester formed from one fatty acid and one aliphatic monohydric alcohol), and in a system comprising $N_i$ molecules with molecular weight $M_i$ (i=1, or i=1, 2 . . . ), it refers to $M_w$ determined by the following formula.

$$M_w = \Sigma N_i M_i^2 / \Sigma N_i M_i$$

As used herein, the weight-average molecular weights are the values measured by gel permeation chromatography (GPC), based on polystyrene.

The GPC measuring conditions may be the following, for example.

Device: Lachrom Elite high-speed liquid chromatogram by Hitachi High-Technologies Corp.
Columns: SHODEX KF-801, KF-803 and KF-804, by Showa Denko K.K.
Eluent: THF
Flow rate: 1.0 mL/min
Driving volume: 100 μL
Detection: RI (differential refractometer)

The weight-average molecular weights listed in the examples of the present specification were measured under the conditions described below.

The blood slipping agent can have an IOB of about 0.00 to about 0.60.

The IOB (Inorganic Organic Balance) is an indicator of the hydrophilic-lipophilic balance, and as used herein, it is the value calculated by the following formula by Oda et al.:

IOB=inorganic value/organic value.

The inorganic value and the organic value are based on the organic paradigm described in "Organic compound predictions and organic paradigms" by Fujita A., Kagaku no Ryoiki (Journal of Japanese Chemistry), Vol. 11, No. 10 (1957) p. 719-725.

The organic values and inorganic values of major groups, according to Fujita, are summarized in Table 1 below.

TABLE 1

| Group | Inorganic value | Organic value |
|---|---|---|
| —COOH | 150 | 0 |
| —OH | 100 | 0 |
| —O—CO—O— | 80 | 0 |
| —CO— | 65 | 0 |
| —COOR | 60 | 0 |
| —O— | 20 | 0 |
| Triple bond | 3 | 0 |
| Double bond | 2 | 0 |
| $CH_2$ | 0 | 20 |
| iso-branch | 0 | −10 |
| tert-branch | 0 | −20 |
| Light metal (salt) | ≥500 | 0 |
| Heavy metal (salt), amine, $NH_3$ salt | ≥400 | 0 |

For example, in the case of an ester of tetradecanoic acid which has 14 carbon atoms and dodecyl alcohol which has 12 carbon atoms, the organic value is 520 ($CH_2$, 20×26) and the inorganic value is 60 (—COOR, 60×1), and therefore IOB=0.12.

The IOB of the blood slipping agent is preferably between about 0.00 and 0.60, more preferably between about 0.00 and 0.50, even more preferably between about 0.00 and 0.40 and most preferably between about 0.00 and 0.30. If the IOB is within this range, it will be easier to meet the aforementioned conditions for the water-holding capacity and kinematic viscosity.

The blood slipping agent preferably has a melting point of about 45° C. or less, and more preferably it has a melting point of about 40° C. or less. If the blood slipping agent has a melting point of about 45° C. or less, the blood slipping agent will more easily exhibit a kinematic viscosity in the aforementioned range.

As used herein, the term "melting point" refers to the peak top temperature for the endothermic peak during conversion from solid to liquid, upon measurement with a differential scanning calorimetry analyzer at a temperature-elevating rate of 10° C./min. The melting point may be measured using a Model DSC-60 DSC measuring apparatus by Shimadzu Corp., for example.

If the blood slipping agent has a melting point of about 45° C. or less, it may be either liquid or solid at room temperature (25° C.), or in other words, the melting point may be either about 25° C. or higher or below about 25° C., and for example, it may have a melting point of about −5° C. or about −20° C. The reason for a melting point of about 45° C. or less for the blood slipping agent will be explained below.

The blood slipping agent does not have a lower limit for the melting point thereof, but the vapor pressure is preferably low. The vapor pressure of the blood slipping agent is preferably about 0-200 Pa, more preferably about 0-100 Pa, even more preferably about 0-10 Pa, even more preferably about 0-1 Pa, and even more preferably about 0.0-0.1 Pa at 25° C. (1 atmosphere).

Considering that the absorbent article of the present disclosure is to be used in contact with the human body, the vapor pressure is preferably about 0-700 Pa, more preferably about 0-100 Pa, even more preferably about 0-10 Pa, even more preferably about 0-1 Pa, and even more preferably 0.0-0.1 Pa, at 40° C. (1 atmosphere). If the vapor pressure of the blood slipping agent is high, gasification may occur during storage and the amount may be reduced, often creating problems, such as odor during wear.

The melting point of the blood slipping agent may be selected depending on the weather or duration of wear. For example, in regions with a mean atmospheric temperature of about 10° C. or less, using a blood slipping agent with a melting point of about 10° C. or less helps the blood slipping agent function after excretion of menstrual blood, even if it has been cooled by the ambient temperature.

Also, when the absorbent article is to be used for a prolonged period of time, the melting point of the blood slipping agent is preferably at the high end of the range of about 45° C. or less. This is so that the blood slipping agent will not be easily affected by sweat or friction during wearing, and will not easily become biased even during prolonged wearing.

In the technical field, the skin contact surfaces of top sheets are coated with surfactants in order to alter the surface tension of menstrual blood and promote rapid absorption of menstrual blood. However, a top sheet coated with a surfactant has very high affinity for the hydrophilic components (blood plasma, etc.) in menstrual blood, and acts to attract them, tending to cause menstrual blood instead to remain on the top sheet. The blood slipping agent, unlike conventionally known surfactants, does not have excessively high affinity with menstrual blood and therefore does not cause residue of menstrual blood on the top sheet and allows rapid migration into the absorbent body.

Preferably, the blood slipping agent is selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety.

As used herein, "hydrocarbon" refers to a compound composed of carbon and hydrogen, and it may be a chain hydrocarbon, such as a paraffinic hydrocarbon (containing no double bond or triple bond, also referred to as alkane), an olefin-based hydrocarbon (containing one double bond, also referred to as alkene), an acetylene-based hydrocarbon (containing one triple bond, also referred to as alkyne), or a hydrocarbon comprising two or more bonds selected from the group consisting of double bonds and triple bonds, and cyclic hydrocarbon, such as aromatic hydrocarbons and alicyclic hydrocarbons.

Preferred as such hydrocarbons are chain hydrocarbons and alicyclic hydrocarbons, with chain hydrocarbons being more preferred, paraffinic hydrocarbons, olefin-based hydrocarbons and hydrocarbons with two or more double bonds (containing no triple bond) being more preferred, and paraffinic hydrocarbons being even more preferred.

Chain hydrocarbons include linear hydrocarbons and branched hydrocarbons.

When two or more oxy groups (—O—) are inserted in the compounds of (ii) and (iii) above, the oxy groups (—O—) are not adjacent each other. Thus, compounds (ii) and (iii) do not include compounds with continuous oxy groups (i.e., peroxides).

In the compounds of (iii), compounds in which at least one hydrogen on the hydrocarbon moiety is substituted with a hydroxyl group (—OH) are preferred over compounds in which at least one hydrogen on the hydrocarbon moiety is substituted with a carboxyl group (—COOH). This is because the carboxyl groups bond with metals and the like in menstrual blood, increasing the water holding percentage of the blood slipping agent, which may sometimes exceed the prescribed range. The same is true from the viewpoint of the IOB as well. As shown in Table 1, the carboxyl groups bond with metals and the like in menstrual blood, drastically increasing the inorganic value from 150 to 400 or greater, and therefore a blood slipping agent with carboxyl groups can increase the IOB value to more than about 0.60 during use.

More preferably, the blood slipping agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety.

When 2 or more same or different bonds are inserted in the compound of (ii') or (iii'), i.e., when 2 or more same or different bonds selected from the group consisting carbonyl bonds (—CO—), ester bonds (—COO—), carbonate bonds (—OCOO—) and ether bonds (—O—) are inserted, the bonds are not adjacent to each other, and at least one carbon atom lies between each of the bonds.

The blood slipping agent has more preferably about 1.8 or less carbonyl bonds (—CO—), about 2 or less ester bonds (—COO—), about 1.5 or less carbonate bonds (—OCOO—), about 6 or less ether bonds (—O—), about 0.8 or less carboxyl groups (—COOH) and/or about 1.2 or less hydroxyl groups (—OH), per 10 carbon atoms in the hydrocarbon moiety.

Even more preferably, the blood slipping agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

The blood slipping agent in accordance with (A) to (F) will now be described in detail.

[(A) Ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety]

In the (A) ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety (hereunder also referred to as "compound (A)"), it is not necessary for all of the hydroxyl groups to be esterified so long as the kinematic viscosity, water holding percentage and weight-average molecular weight are within the aforementioned ranges.

Examples of (A1) a compound having a chain hydrocarbon moiety and 2-4 hydroxyl groups substituting for hydrogens on the chain hydrocarbon moiety (hereunder also referred to as "compound (A1)") include chain hydrocarbon tetraols, such as alkanetetraols, including pentaerythritol, chain hydrocarbon triols, such as alkanetriols, including glycerins, and chain hydrocarbon diols, such as alkanediols, including glycols.

Examples of (A2) a compound having a chain hydrocarbon moiety and 1 carboxyl group substituting for a hydrogen on the chain hydrocarbon moiety include compounds in which one hydrogen on the hydrocarbon is substituted with one carboxyl group (—COOH), such as fatty acids.

Examples for compound (A) include ($a_1$) an ester of a chain hydrocarbon tetraol and at least one fatty acid, ($a_2$) an ester of a chain hydrocarbon triol and at least one fatty acid, and ($a_3$) an ester of a chain hydrocarbon diol and at least one fatty acids.

[($a_1$) Esters of a Chain Hydrocarbon Tetraol and at Least One Fatty Acid]

Examples of an ester of a chain hydrocarbon tetraol and at least one fatty acid include tetraesters of pentaerythritol and fatty acids, represented by the following formula (1):

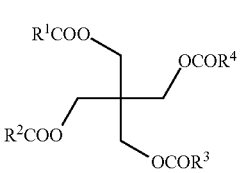

(1)

triesters of pentaerythritol and fatty acids, represented by the following formula (2):

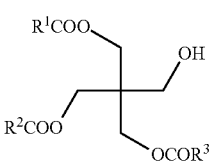

(2)

diesters of pentaerythritol and fatty acids, represented by the following formula (3):

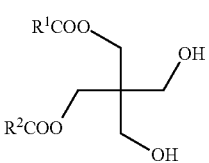

(3)

and monoesters of pentaerythritol and fatty acids, represented by the following formula (4).

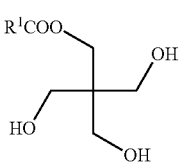

(4)

In the formulas, $R^1$-$R^4$ each represent a chain hydrocarbon.

The fatty acids consisting of the esters of pentaerythritol and fatty acids ($R^1$COOH, $R^2$COOH, $R^3$COOH, and $R^4$COOH) are not particularly restricted so long as the pentaerythritol and fatty acid esters satisfy the conditions for the kinematic viscosity, water holding percentage and weight-average molecular weight, and for example, there may be mentioned saturated fatty acids, such as a $C_2$-$C_{30}$ saturated fatty acids, including acetic acid ($C_2$) ($C_2$ representing the number of carbons, corresponding to the number of carbons of each of $R^1C$, $R^2C$, $R^3C$ or $R^4C$, same hereunder), propanoic acid ($C_3$), butanoic acid ($C_4$) and isomers thereof, such as 2-methylpropanoic acid ($C_4$), pentanoic acid ($C_5$) and isomers thereof, such as 2-methylbutanoic acid ($C_5$) and 2,2-dimethylpropanoic acid ($C_5$), hexanoic acid ($C_6$), heptanoic acid ($C_7$), octanoic acid ($C_8$) and isomers thereof, such as 2-ethylhexanoic acid ($C_8$), nonanoic acid ($C_9$), decanoic acid ($C_{10}$), dodecanoic acid ($C_{12}$), tetradecanoic acid ($C_{14}$), hexadecanoic acid ($C_{16}$), heptadecanoic acid ($C_{17}$), octadecanoic acid ($C_{18}$), eicosanoic acid ($C_{20}$), docosanoic acid ($C_{22}$), tetracosanoic acid ($C_{24}$), hexacosanoic acid ($C_{26}$), octacosanoic acid ($C_{28}$), triacontanoic acid ($C_{30}$), as well as isomers thereof which are not described above.

The fatty acid may also be an unsaturated fatty acid. Examples of unsaturated fatty acids include $C_3$-$C_{20}$ unsaturated fatty acids, such as monounsaturated fatty acids including crotonic acid ($C_4$), myristoleic acid ($C_{14}$), palmitoleic acid ($C_{16}$), oleic acid ($C_{18}$), elaidic acid ($C_{18}$), vaccenic acid ($C_{18}$), gadoleic acid ($C_{20}$) and eicosenoic acid ($C_{20}$), di-unsaturated fatty acids including linolic acid ($C_{18}$) and eicosadienoic acid ($C_{20}$), tri-unsaturated fatty acids including linolenic acids, such as α-linolenic acid ($C_{18}$) and γ-linolenic acid ($C_{18}$), pinolenic acid ($C_{18}$), eleostearic acids, such as α-eleostearic acid ($C_{18}$) and β-eleostearic acid ($C_{18}$), Mead acid ($C_{20}$), dihomo-γ-linolenic acid ($C_{20}$) and eicosatrienoic acid ($C_{20}$), tetra-unsaturated fatty acids including stearidonic acid ($C_{20}$), arachidonic acid ($C_{20}$) and eicosatetraenoic acid ($C_{20}$), penta-unsaturated fatty acids including bosseopentaenoic acid ($C_{18}$) and eicosapentaenoic acid ($C_{20}$), and partial hydrogen adducts of the foregoing.

Considering the potential for degradation by oxidation and the like, the ester of pentaerythritol and a fatty acid is preferably an ester of pentaerythritol and a fatty acid, which is derived from a saturated fatty acid, i.e., an ester of pentaerythritol and a saturated fatty acid.

Also, from the viewpoint of lowering the water holding percentage, the ester of pentaerythritol and a fatty acid is preferably a diester, triester or tetraester, more preferably a triester or tetraester, and even more preferably a tetraester.

From the viewpoint of the IOB being from about 0.00 to about 0.60, in a tetraester of pentaerythritol and a fatty acid, the total number of carbons of the fatty acid composing the tetraester of the pentaerythritol and fatty acid, i.e. the total number of carbons of the $R^1C$, $R^2C$, $R^3C$ and $R^4C$ portions in formula (1), is preferably about 15 (the IOB is 0.60 when the total number of carbon atoms is 15).

Examples of tetraesters of pentaerythritol and fatty acids include tetraesters of pentaerythritol with hexanoic acid ($C_6$), heptanoic acid ($C_7$), octanoic acid ($C_8$), such as 2-ethylhexanoic acid ($C_8$), nonanoic acid ($C_9$), decanoic acid ($C_{10}$) and/or dodecanoic acid ($C_{12}$).

From the viewpoint of the IOB being from about 0.00 to about 0.60, in a triester of pentaerythritol and a fatty acid, the total number of carbons of the fatty acid composing the triester of the pentaerythritol and fatty acid, i.e. the total number of carbons of the $R^1C$, $R^2C$ and $R^3C$ portions in formula (2), is preferably about 19 or greater (the IOB is 0.58 when the number of carbon atoms is 19).

From the viewpoint of the IOB being from about 0.00 to about 0.60, in a diester of pentaerythritol and a fatty acid, the total number of carbons of the fatty acid composing the diester of the pentaerythritol and fatty acid, i.e. the total number of carbons of the $R^1C$ and $R^2C$ portion in formula (3), is preferably about 22 or greater (the IOB is 0.59 when the number of carbon atoms is 22).

From the viewpoint of the IOB being from about 0.00 to about 0.60, in a monoester of pentaerythritol and a fatty acid, the total number of carbons of the fatty acid composing the monoester of the pentaerythritol and fatty acid, i.e. the number of carbons of the $R^1C$ portion in formula (4), is preferably about 25 or greater (the IOB is 0.60 when the number of carbon atoms is 25).

The effects of double bonds, triple bonds, iso-branches and tert-branches are not considered in this calculation of the IOB (same hereunder).

Commercial products which are esters of pentaerythritol and fatty acids include UNISTAR H-408BRS and H-2408BRS-22 (mixed product) (both products of NOF Corp.).

[(a2) Ester of a Chain Hydrocarbon Triol and at Least One Fatty Acid]

Examples of esters of a chain hydrocarbon triol and at least one fatty acid include triesters of glycerin and fatty acids, represented by formula (5):

diesters of glycerin and fatty acids, represented by the following formula (6):

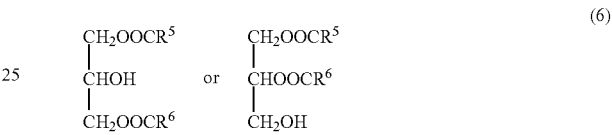

and monoesters of glycerin and fatty acids, represented by the following formula (7):

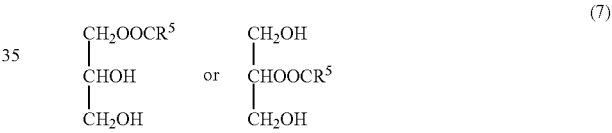

wherein $R^5$-$R^7$ each represent a chain hydrocarbon.

The fatty acid consisting of the ester of glycerin and a fatty acid ($R^5COOH$, $R^6COOH$ and $R^7COOH$) is not particularly restricted so long as the ester of glycerin and a fatty acid satisfies the conditions for the kinematic viscosity, water holding percentage and weight-average molecular weight, and for example, there may be mentioned the fatty acids mentioned for the "($a_1$) Ester of a chain hydrocarbon tetraol and at least one fatty acid", namely saturated fatty acids and unsaturated fatty acids, and in consideration of the potential for degradation by oxidation and the like, the ester is preferably a glycerin and fatty acid ester, which is derived from a saturated fatty acid, i.e., an ester of glycerin and a saturated fatty acid.

Also, from the viewpoint of lowering the water holding percentage and result in greater hydrophobicity, the ester of glycerin and a fatty acid is preferably a diester or triester, and more preferably a triester.

A triester of glycerin and a fatty acid is also known as a triglyceride, and examples include triesters of glycerin and octanoic acid ($C_8$), triesters of glycerin and decanoic acid ($C_{10}$), triesters of glycerin and dodecanoic acid ($C_{12}$), triesters of glycerin and 2 or more different fatty acids, and mixtures of the foregoing.

Examples of triesters of glycerin and 2 or more fatty acids include triesters of glycerin with octanoic acid ($C_8$) and decanoic acid ($C_{10}$), triesters of glycerin with octanoic acid ($C_8$), decanoic acid ($C_{10}$) and dodecanoic acid ($C_{12}$), and triesters of glycerin with octanoic acid ($C_8$), decanoic acid ($C_{10}$), dodecanoic acid ($C_{12}$), tetradecanoic acid ($C_{14}$), hexadecanoic acid ($C_{16}$) and octadecanoic acid ($C_{18}$).

In order to obtain a melting point of about 45° C. or less, preferred triesters of glycerin and fatty acids are those with about 40 or less as the total number of carbons of the fatty acid consisting of the triester of glycerin and the fatty acid, i.e., the total number of carbons of the $R^5C$, $R^6C$ and $R^7C$ sections in formula (5).

From the viewpoint of the IOB being from about 0.00 to about 0.60, in a triester of glycerin and a fatty acid, the total number of carbons of the fatty acid composing the triester of the glycerin and fatty acid, i.e. the total number of carbons of the $R^5C$, $R^6C$ and $R^7C$ portions in formula (5), is preferably about 12 or greater (the IOB is 0.60 when the total number of carbon atoms is 12).

Triesters of glycerin and fatty acids, being aliphatic and therefore potential constituent components of the human body, are preferred from the viewpoint of safety.

Commercial products of triesters of glycerin and fatty acids include tri-coconut fatty acid glycerides, NA36, PANACET 800, PANACET 800B and PANACET 810S, and tri-C2L oil fatty acid glycerides and tri-CL oil fatty acid glycerides (all products of NOF Corp.).

A diester of glycerin and a fatty acid is also known as a diglyceride, and examples include diesters of glycerin and decanoic acid ($C_{10}$), diesters of glycerin and dodecanoic acid ($C_{12}$), diesters of glycerin and hexadecanoic acid ($C_{16}$), diesters of glycerin and 2 or more different fatty acids, and mixtures of the foregoing.

From the viewpoint of the IOB being from about 0.00 to about 0.60, in a diester of glycerin and a fatty acid, the total number of carbons of the fatty acid composing the diester of the glycerin and fatty acid, i.e. the total number of carbons of the $R^5C$ and $R^6C$ portions in formula (6), is preferably about 16 or greater (the IOB is 0.58 when the total number of carbon atoms is 16).

Monoesters of glycerin and fatty acids are also known as monoglycerides, and examples include glycerin and octadecanoic acid ($C_{18}$) monoester, and glycerin and docosanoic acid ($C_{22}$) monoester.

From the viewpoint of the IOB being from about 0.00 to about 0.60, in a monoester of glycerin and a fatty acid, the total number of carbons of the fatty acid composing the monoester of the glycerin and fatty acid, i.e. the number of carbons of the $R^5C$ portion in formula (7), is preferably about 19 or greater (the IOB is 0.59 when the number of carbon atoms is 19).

[($a_3$) Ester of a Chain Hydrocarbon Diol and at Least One Fatty Acid]

Examples of an ester of a chain hydrocarbon diol and at least one fatty acid include monoesters and diesters of fatty acids with $C_2$-$C_6$ chain hydrocarbon diols, such as $C_2$-$C_6$ glycols, including ethylene glycol, propylene glycol, butylene glycol, pentylene glycol and hexylene glycol.

Specifically, examples of an ester of a chain hydrocarbon diol and at least one fatty acid include diesters of $C_2$-$C_6$ glycols and fatty acids, represented by the following formula (8):

wherein k represents an integer of 2-6, and $R^8$ and $R^9$ each represent a chain hydrocarbon, and monoesters of $C_2$-$C_6$ glycols and fatty acids, represented by the following formula (9):

wherein k represents an integer of 2-6, and $R^8$ is a chain hydrocarbon.

The fatty acid to be esterified in an ester of a $C_2$-$C_6$ glycol and a fatty acid (corresponding to $R^8COOH$ and $R^9COOH$ in formula (8) and formula (9)) is not particularly restricted so long as the ester of the $C_2$-$C_6$ glycol and fatty acid satisfies the conditions for the kinematic viscosity, water holding percentage and weight-average molecular weight, and for example, there may be mentioned the fatty acids mentioned above for the "($a_1$) Ester of a chain hydrocarbon tetraol and at least one fatty acid", namely saturated fatty acids and unsaturated fatty acids, and in consideration of the potential for degradation by oxidation and the like, it is preferably a saturated fatty acid.

From the viewpoint of the IOB being from about 0.00 to about 0.60, in a diester of butylene glycol represented by formula (8) (k=4) and a fatty acid, the total number of carbons of the $R^8C$ and $R^9C$ portions is preferably about 6 or greater (the IOB is 0.60 when the total number of carbon atoms is 6).

From the viewpoint of the IOB being from about 0.00 to about 0.60, in a monoester of ethylene glycol represented by formula (9) (k=2) and a fatty acid, the number of carbons of the $R^8C$ portion is preferably about 12 or greater (the IOB is 0.57 when the number of carbon atoms is 12).

Considering the potential for degradation by oxidation and the like, the ester of the $C_2$-$C_6$ glycol and fatty acid is preferably a $C_2$-$C_6$ glycol and fatty acid ester derived from a saturated fatty acid, or in other words, an ester of a $C_2$-$C_6$ glycol and a saturated fatty acid.

Also, from the viewpoint of lowering the water holding percentage, the ester of the $C_2$-$C_6$ glycol and fatty acid is preferably a glycol and fatty acid ester derived from a glycol with a greater number of carbons, such as an ester of a glycol and a fatty acid derived from butylene glycol, pentylene glycol or hexylene glycol.

Also, from the viewpoint of lowering the water holding percentage, the ester of a $C_2$-$C_6$ glycol and fatty acid is preferably a diester.

Examples of commercial products of esters of $C_2$-$C_6$ glycols and fatty acids include COMPOL BL and COMPOL BS (both products of NOF Corp.).

[(B) Ether of (B1) a Compound Having a Chain Hydrocarbon Moiety and 2-4 Hydroxyl Groups Substituting for Hydrogens on the Chain Hydrocarbon Moiety and (B2) a Compound Having a Chain Hydrocarbon Moiety and 1 Hydroxyl Group Substituting for a Hydrogen on the Chain Hydrocarbon Moiety]

In the (B) ether of (B1) a compound having a chain hydrocarbon moiety and 2-4 hydroxyl groups substituting for hydrogens on the chain hydrocarbon moiety and (B2) a compound having a chain hydrocarbon moiety and 1 hydroxyl group substituting for a hydrogen on the chain hydrocarbon moiety (hereunder also referred to as "compound (B)"), it is not necessary for all of the hydroxyl groups to be etherified so long as the kinematic viscosity, water holding percentage and weight-average molecular weight are within the aforementioned ranges.

Examples of (B1) a compound having a chain hydrocarbon moiety and 2-4 hydroxyl groups substituting for hydrogens on the chain hydrocarbon moiety (hereunder also referred to as "compound (B1)") include those mentioned for "compound (A)" as compound (A1), such as pentaerythritol, glycerin and glycol.

Examples of (B2) a compound having a chain hydrocarbon moiety and 1 hydroxyl group substituting for a hydrogen on the chain hydrocarbon moiety (hereunder also referred to as "compound (B2)") include compounds wherein 1 hydrogen on the hydrocarbon is substituted with 1 hydroxyl group (—OH), such as aliphatic monohydric alcohols, including saturated aliphatic monohydric alcohols and unsaturated aliphatic monohydric alcohols.

Examples of saturated aliphatic monohydric alcohols include $C_1$-$C_{20}$ saturated aliphatic monohydric alcohols, such as methyl alcohol ($C_1$) ($C_1$ representing the number of carbon atoms, same hereunder), ethyl alcohol ($C_2$), propyl alcohol ($C_3$) and isomers thereof, including isopropyl alcohol ($C_3$), butyl alcohol ($C_4$) and isomers thereof, including sec-butyl alcohol ($C_4$) and tert-butyl alcohol ($C_4$), pentyl alcohol ($C_5$), hexyl alcohol ($C_6$), heptyl alcohol ($C_7$), octyl alcohol ($C_8$) and isomers thereof, including 2-ethylhexyl alcohol ($C_8$), nonyl alcohol ($C_9$), decyl alcohol ($C_{10}$), dodecyl alcohol ($C_{12}$), tetradecyl alcohol ($C_{14}$), hexadecyl alcohol ($C_{16}$), heptadecyl alcohol ($C_{17}$), octadecyl alcohol ($C_{18}$) and eicosyl alcohol ($C_{20}$), as well as their isomers other than those mentioned.

Unsaturated aliphatic monohydric alcohols include those wherein 1 C—C single bond of a saturated aliphatic monohydric alcohol mentioned above is replaced with a C═C double bond, such as oleyl alcohol, and for example, such alcohols are commercially available by New Japan Chemical Co., Ltd. as the RIKACOL Series and UNJECOL Series.

Examples for compound (B) include ($b_1$) an ether of a chain hydrocarbon tetraol and at least one aliphatic monohydric alcohol, such as monoethers, diethers, triethers and tetraethers, preferably diethers, triethers and tetraethers, more preferably triethers and tetraethers and even more preferably tetraethers, ($b_2$) an ether of a chain hydrocarbon triol and at least one aliphatic monohydric alcohol, such as monoethers, diethers and triethers, preferably diethers and triethers and more preferably triethers, and ($b_3$) an ether of a chain hydrocarbon diol and at least one aliphatic monohydric alcohol, such as monoethers and diethers, and preferably diethers.

Examples of an ether of a chain hydrocarbon tetraol and at least one aliphatic monohydric alcohol include tetraethers, triethers, diethers and monoethers of pentaerythritol and aliphatic monohydric alcohols, represented by the following formulas (10)-(13):

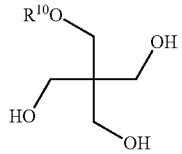
(10)

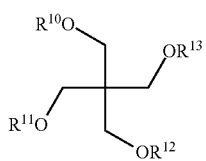
(11)

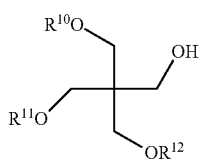
(12)

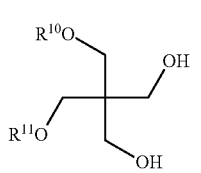
(13)

wherein $R^{10}$-$R^{13}$ each represent a chain hydrocarbon.

Examples of an ether of a chain hydrocarbon triol and at least one aliphatic monohydric alcohol include triethers, diethers and monoethers of glycerin and aliphatic monohydric alcohols, represented by the following formulas (14)-(16):

(14)

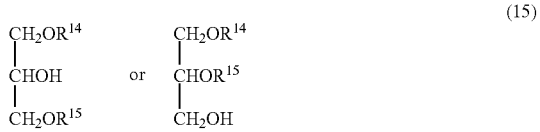
(15)

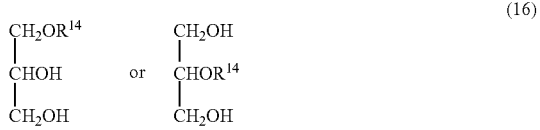
(16)

wherein $R^{14}$-$R^{16}$ each represent a chain hydrocarbon.

Examples of an ether of a chain hydrocarbon diol and at least one aliphatic monohydric alcohol include diethers of $C_2$-$C_6$ glycols and aliphatic monohydric alcohols, represented by the following formula (17):

$$R^{17}OC_nH_{2n}OR^{18} \quad (17)$$

wherein n is an integer of 2-6, and $R^{17}$ and $R^{18}$ are each a chain hydrocarbon, and monoethers of $C_2$-$C_6$ glycols and aliphatic monohydric alcohols, represented by the following formula (18):

$$R^{17}OC_nH_{2n}OH \quad (18)$$

wherein n is an integer of 2-6, and $R^{17}$ is a chain hydrocarbon.

From the viewpoint of the IOB being between about 0.00 and about 0.60, in a tetraether of pentaerythritol and an aliphatic monohydric alcohol, the total number of carbon atoms of the aliphatic monohydric alcohol composing the tetraether of pentaerythritol and the aliphatic monohydric alcohol, i.e. the total number of carbon atoms of the $R^{10}$, $R^{11}$, $R^{12}$ and $R^{13}$ portions in formula (10), is preferably about 4 or greater (the IOB is 0.44 when the total number of carbon atoms is 4).

From the viewpoint of the IOB being between about 0.00 and about 0.60, in a triether of pentaerythritol and an aliphatic monohydric alcohol, the total number of carbon atoms of the aliphatic monohydric alcohol composing the triether of pentaerythritol and the aliphatic monohydric alcohol, i.e. the total number of carbon atoms of the $R^{10}$, $R^{11}$ and $R^{12}$ portions in formula (11), is preferably about 9 or greater (the IOB is 0.57 when the total number of carbon atoms is 9).

From the viewpoint of the IOB being between about 0.00 and about 0.60, in a diether of pentaerythritol and an aliphatic monohydric alcohol, the total number of carbon atoms of the aliphatic monohydric alcohol composing the diether of pentaerythritol and the aliphatic monohydric alcohol, i.e. the total number of carbon atoms of the $R^{10}$ and $R^{11}$ portions in formula (12), is preferably about 15 or greater (the IOB is 0.60 when the total number of carbon atoms is 15).

From the viewpoint of the IOB being between about 0.00 and about 0.60, in a monoether of pentaerythritol and an aliphatic monohydric alcohol, the number of carbon atoms of the aliphatic monohydric alcohol composing the monoether of pentaerythritol and the aliphatic monohydric alcohol, i.e. the number of carbon atoms of the $R^{10}$ portion in formula (13), is preferably about 22 or greater (the IOB is 0.59 when the number of carbon atoms is 22).

From the viewpoint of the IOB being between about 0.00 and about 0.60, in a triether of glycerin and an aliphatic monohydric alcohol, the total number of carbon atoms of the aliphatic monohydric alcohol composing the triether of glycerin and the aliphatic monohydric alcohol, i.e. the total number of carbon atoms of the $R^{14}$, $R^{15}$ and $R^{16}$ portions in formula (14), is preferably about 3 or greater (the IOB is 0.50 when the total number of carbon atoms is 3).

From the viewpoint of the IOB being between about 0.00 and about 0.60, in a diether of glycerin and an aliphatic monohydric alcohol, the total number of carbon atoms of the aliphatic monohydric alcohol composing the diether of glycerin and the aliphatic monohydric alcohol, i.e. the total number of carbon atoms of the $R^{14}$ and $R^{15}$ portions in formula (15), is preferably about 9 or greater (the IOB is 0.58 when the total number of carbon atoms is 9).

From the viewpoint of the IOB being between about 0.00 and about 0.60, in a monoether of glycerin and an aliphatic monohydric alcohol, the number of carbon atoms of the aliphatic monohydric alcohol composing the monoether of glycerin and the aliphatic monohydric alcohol, i.e. the number of carbon atoms of the $R^{14}$ portion in formula (16), is preferably 16 or greater (the IOB is 0.58 when the number of carbon atoms is 16).

From the viewpoint of the IOB being from about 0.00 to about 0.60, in a diether of butylene glycol represented by formula (17) (n=4) and an aliphatic monohydric alcohol, the total number of carbon atoms of the $R^{17}$ and $R^{18}$ portions is preferably about 2 or greater (the IOB is 0.33 when the total number of carbon atoms is 2).

From the viewpoint of the IOB being from about 0.00 to about 0.60, in a monoether of ethylene glycol represented by formula (18) (n=2) and an aliphatic monohydric alcohol, the number of carbon atoms of the $R^{17}$ portion is preferably about 8 or greater (the IOB is 0.60 when the number of carbon atoms is 8).

Compound (B) may be produced by dehydrating condensation of compound (B1) and compound (B2) in the presence of an acid catalyst.

[(C) Ester of (C1) a Carboxylic Acid, Hydroxy Acid, Alkoxy Acid or Oxoacid Comprising a Chain Hydrocarbon Moiety and 2-4 Carboxyl Groups Substituting for Hydrogens on the Chain Hydrocarbon Moiety and (C2) a Compound Having a Chain Hydrocarbon Moiety and 1 Hydroxyl Group Substituting for a Hydrogen on the Chain Hydrocarbon Moiety]

In the (C) ester of (C1) a carboxylic acid, hydroxy acid, alkoxy acid or oxoacid comprising a chain hydrocarbon moiety and 2-4 carboxyl groups substituting for hydrogens on the chain hydrocarbon moiety and (C2) a compound having a chain hydrocarbon moiety and 1 hydroxyl group substituting for a hydrogen on the chain hydrocarbon moiety (hereunder also referred to as "compound (C)"), it is not necessary for all of the carboxyl groups to be esterified so long as the kinematic viscosity, water holding percentage and weight-average molecular weight are within the aforementioned ranges.

Examples of (C1) a carboxylic acid, hydroxy acid, alkoxy acid or oxoacid comprising a chain hydrocarbon moiety and 2-4 carboxyl groups substituting for hydrogens on the chain hydrocarbon moiety (hereunder also referred to as "compound (C1)") include chain hydrocarbon carboxylic acids with 2-4 carboxyl groups, such as chain hydrocarbon dicarboxylic acids including alkanedicarboxylic acids, such as ethanedioic acid, propanedioic acid, butanedioic acid, pentanedioic acid, hexanedioic acid, heptanedioic acid, octanedioic acid, nonanedioic acid and decanedioic acid, chain hydrocarbon tricarboxylic acids, including alkanetricarboxylic acids, such as propanetrioic acid, butanetrioic acid, pentanetrioic acid, hexanetrioic acid, heptanetrioic acid, octanetrioic acid, nonanetrioic acid and decanetrioic acid, and chain hydrocarbon tetracarboxylic acids, including alkanetetracarboxylic acids, such as butanetetraoic acid, pentanetetraoic acid, hexanetetraoic acid, heptanetetraoic acid, octanetetraoic acid, nonanetetraoic acid and decanetetraoic acid.

Compound (C1) includes chain hydrocarbon hydroxy acids with 2-4 carboxyl groups, such as malic acid, tartaric acid, citric acid and isocitric acid, chain hydrocarbon alkoxy acids with 2-4 carboxyl groups, such as O-acetylcitric acid, and chain hydrocarbon oxoacids with 2-4 carboxyl groups.

(C2) Compound having a chain hydrocarbon moiety and 1 hydroxyl group substituting for a hydrogen on the chain hydrocarbon moiety includes those mentioned for "compound (B)", such as aliphatic monohydric alcohols.

Compound (C) may be ($c_1$) an ester, for example a monoester, diester, triester or tetraester, preferably a diester, triester or tetraester, more preferably a triester or tetraester and even more preferably a tetraester, of a chain hydrocarbon tetracarboxylic acid, hydroxy acid, alkoxy acid or oxoacid with 4 carboxyl groups, and at least one aliphatic monohydric alcohol, ($c_2$) an ester, for example, a monoester, diester or triester, preferably a diester or triester and more preferably a triester, of a chain hydrocarbon tricarboxylic acid, hydroxy acid, alkoxy acid or oxoacid with 3 carboxyl groups, and at least one aliphatic monohydric alcohol, or ($c_3$) an ester, for example, a monoester or diester, and preferably a diester, of a chain hydrocarbon dicarboxylic acid, hydroxy acid, alkoxy acid or oxoacid with 2 carboxyl groups, and at least one aliphatic monohydric alcohol.

Examples for compound (C) include dioctyl adipate, diisostearyl malate, tributyl citrate and tributyl O-acetylcitrate, of which commercially available products exist.

[(D) Compound Having a Chain Hydrocarbon Moiety and One Bond Selected from the Group Consisting of an Ether Bond (—O—), Carbonyl Bond (—CO—), Ester Bond (—COO—) and Carbonate Bond (—OCOO—) Inserted Between a C—C Single Bond of the Chain Hydrocarbon Moiety]

The (D) compound having a chain hydrocarbon moiety and one bond selected from the group consisting of an ether bond (—O—), carbonyl bond (—CO—), ester bond (—COO—) and carbonate bond (—OCOO—) inserted between a C—C single bond of the chain hydrocarbon moiety (hereunder also referred to as "compound (D)") may be ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, or ($d_4$) a dialkyl carbonate.

[($d_1$) Ether of an Aliphatic Monohydric Alcohol and an Aliphatic Monohydric Alcohol]

Ethers of an aliphatic monohydric alcohol and an aliphatic monohydric alcohol include compounds having the following formula (19):

$$R^{19}OR^{20} \quad (19)$$

wherein $R^{19}$ and $R^{20}$ each represent a chain hydrocarbon.

The aliphatic monohydric alcohol consisting of the ether (corresponding to $R^{19}OH$ and $R^{20}OH$ in formula (19)) is not particularly restricted so long as the ether satisfies the conditions for the kinematic viscosity, water holding percentage and weight-average molecular weight, and for example, it may be one of the aliphatic monohydric alcohols mentioned for "compound (B)".

[($d_2$) Dialkyl Ketone]

The dialkyl ketone may be a compound of the following formula (20):

$$R^{21}COR^{22} \quad (20)$$

wherein $R^{21}$ and $R^{22}$ are each an alkyl group.

The dialkyl ketone may be a commercially available product, or it may be obtained by a known method, such as by oxidation of a secondary alcohol with chromic acid or the like.

[($d_3$) Ester of a Fatty Acid and an Aliphatic Monohydric Alcohol]

Examples of esters of a fatty acid and an aliphatic monohydric alcohol include compounds having the following formula (21):

$$R^{23}COOR^{24} \quad (21)$$

wherein $R^{23}$ and $R^{24}$ each represent a chain hydrocarbon.

Examples of fatty acids consisting of these esters (corresponding to $R^{23}COOH$ in formula (21)) include the fatty acids mentioned for the "($a_1$) an ester of a chain hydrocarbon tetraol and at least one fatty acids", and specifically these include saturated fatty acids and unsaturated fatty acids, with saturated fatty acids being preferred in consideration of the potential for degradation by oxidation and the like. The aliphatic monohydric alcohol consisting of the ester (corresponding to $R^{24}OH$ in formula (21)) may be one of the aliphatic monohydric alcohols mentioned for "compound (B)".

Examples of esters of such fatty acids and aliphatic monohydric alcohols include esters of dodecanoic acid ($C_{12}$) and dodecyl alcohol ($C_{12}$) and esters of tetradecanoic acid ($C_{14}$) and dodecyl alcohol ($C_{12}$), and examples of commercial products of esters of such fatty acids and aliphatic monohydric alcohols include ELECTOL WE20 and ELECTOL WE40 (both products of NOF Corp.).

[($d_4$) Dialkyl Carbonate]

The dialkyl carbonate may be a compound of the following formula (22):

$$R^{25}OC(=O)OR^{26} \quad (22)$$

wherein $R^{25}$ and $R^{26}$ are each an alkyl group.

The dialkyl carbonate may be a commercially available product, or it may be synthesized by reaction between phosgene and an alcohol, reaction between formic chloride and an alcohol or alcoholate, or reaction between silver carbonate and an alkyl iodide.

From the viewpoint of the water holding percentage and vapor pressure, the weight-average molecular weight is preferably about 100 or greater and more preferably about 200 or greater, for ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, and ($d_4$) a dialkyl carbonate.

If the total number of carbon atoms is about 8 in a ($d_2$) dialkyl ketone, the melting point will be approximately −50° C. and the vapor pressure will be about 230 Pa at 20° C., in the case of 5-nonanone, for example.

[(E) Polyoxy $C_3$-$C_6$ Alkylene Glycol, or Alkyl Ester or Alkyl Ether Thereof]

The (E) polyoxy $C_3$-$C_6$ alkylene glycol, or alkyl ester or alkyl ether thereof (hereunder also referred to as "compound (E)") may be ($e_1$) a polyoxy $C_3$-$C_6$ alkylene glycol, ($e_2$) an ester of a polyoxy $C_3$-$C_6$ alkylene glycol and at least one fatty acid, or ($e_3$) an ether of a polyoxy $C_3$-$C_6$ alkylene glycol and at least one aliphatic monohydric alcohol. These will now be explained.

[($e_1$) Polyoxy $C_3$-$C_6$ Alkylene Glycol]

Polyoxy $C_3$-$C_6$ alkylene glycols refer to i) one or more homopolymers having a unit selected from the group consisting of oxy $C_3$-$C_6$ alkylene units, such as oxypropylene unit, oxybutylene unit, oxypentylene unit and oxyhexylene unit and having hydroxyl groups at both ends, ii) one or more block copolymers having 2 or more units selected from oxy $C_3$-$C_6$ alkylene units described above and oxyhexylene unit and having hydroxyl groups at both ends, or iii) random copolymers having 2 or more units selected from oxy $C_3$-$C_6$ alkylene units described above and having hydroxyl groups at both ends.

The polyoxy $C_3$-$C_6$ alkylene glycol can be represented by the following formula (23):

$$HO—(C_mH_{2m}O)_n—H \quad (23)$$

wherein m represents an integer of 3-6.

The present inventors have found that with polypropylene glycol (corresponding to a homopolymer of formula (23) where m=3), the condition for the water holding percentage is not satisfied when the weight-average molecular weight is less than about 1,000. Therefore, polypropylene glycol homopolymer is not included in the scope of the blood slipping agent described above, and propylene glycol is included in the ($e_1$) polyoxy $C_3$-$C_6$ alkylene glycol only as a copolymer or random polymer with another glycol.

Incidentally, investigation by the present inventors suggests that with polyethylene glycol (corresponding to a homopolymer of formula (23) where m=2), the condition for the kinematic viscosity and water holding percentage cannot be satisfied when the weight-average molecular weight is less than about 1,000.

From the viewpoint of the IOB being about 0.00 to about 0.60, when formula (23) is polybutylene glycol (a homopolymer where m=4), for example, preferably n about 7 (when n=7, the IOB is 0.57).

Examples of commercial products of polyoxy $C_3$-$C_6$ alkylene glycols include UNIOL™ PB-500 and PB-700 (all products of NOF Corp.).

[($e_2$) Ester of a Polyoxy $C_3$-$C_6$ Alkylene Glycol and at Least One Fatty Acid]

Examples of an ester of a polyoxy $C_3$-$C_6$ alkylene glycol and at least one fatty acids include the polyoxy $C_3$-$C_6$ alkylene glycols mentioned for "($e_1$) Polyoxy $C_3$-$C_6$ alkylene glycol" in which one or both OH ends have been esterified with fatty acids, i.e. monoesters and diesters.

Examples of fatty acids to be esterified in the ester of a polyoxy $C_3$-$C_6$ alkylene glycol and at least one fatty acid include the fatty acids mentioned for the "($a_1$) Ester of a chain hydrocarbon tetraol and at least one fatty acid", and specifically these include saturated fatty acids and unsaturated fatty acids, with saturated fatty acids being preferred in consideration of the potential for degradation by oxidation and the like.

[($e_3$) Ether of a Polyoxy $C_3$-$C_6$ Alkylene Glycol and at Least One Aliphatic Monohydric Alcohol]

Examples of an ether of a polyoxy $C_3$-$C_6$ alkylene glycols and at least one aliphatic monohydric alcohol include the polyoxy $C_3$-$C_6$ alkylene glycols mentioned for "($e_1$) Polyoxy $C_3$-$C_6$ alkylene glycol" wherein one or both OH ends have been etherified by an aliphatic monohydric alcohol, i.e. monoethers and diethers.

In an ether of a polyoxy $C_3$-$C_6$ alkylene glycol and at least one aliphatic monohydric alcohol, the aliphatic monohydric alcohol to be etherified may be an aliphatic monohydric alcohol among those mentioned for "compound (B)".

[(F) Chain Hydrocarbon]

Examples of chain hydrocarbons include ($f_1$) chain alkanes, such as straight-chain alkanes and branched chain alkanes. Straight-chain alkanes with melting points of about 45° C. or less have up to about 22 carbon atoms, and at a vapor pressure of 1 atmosphere and about 0.01 Pa or less at 25° C., the number of carbon atoms is 13 or greater. Branched chain alkanes tend to have lower melting points than chain alkanes, given the same number of carbon atoms. Branched chain alkanes may therefore include those with 22 and more carbon atoms, even with melting points of below about 45° C.

Examples of commercially available hydrocarbon products include PARLEAM 6 (NOF Corp.).

In an absorbent article according to one embodiment of the present disclosure the top sheet contains a blood slipping agent, while in an absorbent article according to another embodiment of the present disclosure the top sheet contains only a blood slipping agent, and in an absorbent article according to yet another embodiment of the present disclosure the top sheet contains a blood slipping agent-containing composition that includes a blood slipping agent and at least one other component.

Such a blood slipping agent-containing composition will now be described.

[Blood Slipping Agent-Containing Composition]

The blood slipping agent-containing composition contains a blood slipping agent and at least one other component.

The other component is not particularly restricted so long as it does not inhibit the effect of the present disclosure, and it may be any one commonly employed in absorbent articles of the art, and especially top sheets.

Examples for the other component(s) include silicone oils, silicones, silicone-based resins and the like.

Examples for the other component(s) also include antioxidants, such as BHT (2,6-di-t-butyl-p-cresol), BHA (butylated hydroxyanisole) and propyl gallate.

Further examples for the other component(s) include vitamins, such as natural vitamins and synthetic vitamins. Examples of vitamins include water-soluble vitamins, such as group B vitamins, including vitamin $B_1$, vitamin $B_2$, vitamin $B_3$, vitamin $B_5$, vitamin $B_6$, vitamin $B_7$, vitamin $B_9$ and vitamin $B_{12}$, and vitamin C.

Other examples of vitamins include fat-soluble vitamins, such as group A vitamins, group D vitamins, group E vitamins and group K vitamins.

The derivatives of these vitamins are also included.

Examples for the other component(s) include amino acids, such as alanine, arginine, lysine, histidine, proline and hydroxyproline, and peptides.

Other examples for the other component(s) include zeolite, such as natural zeolite, examples of which include analcite, chabazite, heulandite, natrolite, stilbite and thomosonite, and synthetic zeolite.

Still other examples for the other component(s) include cholesterol, hyaluronic acid, lecithin and ceramide.

Yet other examples for the other component(s) include drugs, such as skin astringents, anti-pimple medications, anti-wrinkle agents, anti-cellulite agents, skin whiteners, antimicrobial agents and antifungal agents.

Examples of skin astringents include zinc oxide, aluminum sulfate, tannic acid and the like, and oil-soluble skin astringents, such as fat-soluble polyphenols. Fat-soluble polyphenols include natural fat-soluble polyphenols, such as barley extract, otogiriso extract, white deadnettle extract, chamomilla extract, burdock extract, *salvia* extract, linden extract, common lime extract, white birch extract, common horsetail extract, sage extract, *salvia* extract, walnut (*J. regia* L. var. *orientalis*) extract, hibiscus extract, loquat leaf extract, Miquel's linden extract, hop extract, common horse-chestnut extract and *coix* seed extract.

Examples of anti-pimple medications include salicylic acid, benzoyl peroxide, resorcinol, sulfur, erythromycin and zinc.

Examples of anti-wrinkle agents include lactic acid, salicylic acid, salicylic acid derivatives, glycolic acid, phytic acid, lipoic acid and lysophosphatidic acid.

Examples of anti-cellulite agents include xanthine compounds, such as aminophylline, caffeine, theophylline and theobromine.

Examples of skin whiteners include niacinamide, kojic acid, arbutin, glucosamine and its derivatives, phytosterol derivatives, and ascorbic acid and its derivatives, as well as mulberry extract and placenta extract.

Examples for the other component(s) also include anti-inflammatory components, pH regulators, antimicrobial agents, humectants, aromatics, pigments, dyes, pigments and plant extracts. Examples of anti-inflammatory components include naturally-derived anti-inflammatory drugs, such as peony, golden grass, otogiriso, chamomile, licorice, peach leaf, Japanese mugwort and *perilla* extract, and synthetic anti-inflammatory drugs, such as allantoin and dipotassium glycyrrhizinate.

Examples of pH regulators include those that keep the skin weakly acidic, such as malic acid, succinic acid, citric acid, tartaric acid and lactic acid.

Titanium oxide is an example of a pigment.

The blood slipping agent-containing composition contains the blood slipping agent and the one or more other components at preferably about 50 to about 99 mass % and about 1 to about 50 mass %, respectively, more preferably about 60 to about 99 mass % and about 1 to about 40 mass %, respectively, even more preferably about 70 to about 99 mass % and about 1 to about 30 mass %, respectively, yet more preferably about 80 to about 99 mass % and about 1 to about 20 mass %, respectively, even yet more preferably about 90 to 99 mass % and about 1 to about 10 mass %, respectively, and even yet more preferably about 95 to 99 mass % and about 1 to about 5 mass %, respectively. These ranges are from the viewpoint of the effect of the present disclosure.

The blood slipping agent-containing composition preferably contains a surfactant in no greater than the amount from hydrophilicizing treatment of the top sheet or second sheet. More specifically, the blood slipping agent-containing composition contains a surfactant in a basis weight range of preferably about 0.0 to about 1.0 g/m$^2$, more preferably about 0.0 to about 0.8 g/m², even more preferably about 0.1 to about 0.5 g/m², and yet more preferably about 0.1 to about 0.3 g/m².

This is because when the amount of surfactant is increased, menstrual blood will tend to be retained in the top sheet. The surfactant, incidentally, has no water holding percentage. This is because there is no layer of the substance to be measured, due to admixture with water.

The blood slipping agent-containing composition contains water in a basis weight range of preferably about 0.0 to about 1.0 g/m², more preferably about 0.0 to about 0.8 g/m², even more preferably about 0.1 to about 0.5 g/m², and yet more preferably about 0.1 to about 0.3 g/m².

Since water lowers the absorption performance of the absorbent article, the amount is preferably low.

Similar to the blood slipping agent, the blood slipping agent-containing composition, as a composition, has at 40° C., a kinematic viscosity of preferably about 0 to about 80 mm²/s, more preferably a kinematic viscosity of about 1 to about 70 mm²/s, even more preferably a kinematic viscosity of about 3 to about 60 mm²/s, yet more preferably a kinematic viscosity of about 5 to about 50 mm²/s, and even yet more preferably a kinematic viscosity of about 7 to about 45 mm²/s.

If the kinematic viscosity of the blood slipping agent-containing composition exceeds 80 mm²/s, the viscosity will increase, and the blood slipping agent composition may not slide down into the interior of the absorbent article as easily with menstrual blood that has reached the skin contact surface of the top sheet.

When the blood slipping agent-containing composition contains a component that is miscible with the blood slipping agent, as at least one other component, the other component preferably has a weight-average molecular weight of less than about 1000, and more preferably a weight-average molecular weight of less than about 900. This is because, if the weight-average molecular weight is about 1000 or higher, tack may result in the blood slipping agent-containing composition itself, tending to create a feeling of unpleasantness for the wearer. If the weight-average molecular weight increases, the viscosity of the blood slipping agent-containing composition will tend to increase, and it will therefore be difficult to lower the viscosity of the blood slipping agent composition by heating to a viscosity suitable for coating, and as a result, the blood slipping agent may need to be diluted with a solvent.

The blood slipping agent-containing composition, as a composition, has a water holding percentage of about 0.01 to about 4.0 mass %, preferably it has a water holding percentage of about 0.02 to about 3.5 mass %, more preferably it has a water holding percentage of about 0.03 to about 3.0 mass %, even more preferably it has a water holding percentage of about 0.04 to about 2.5 mass %, and yet more preferably it has a water holding percentage of about 0.05 to about 2.0 mass %.

A low water holding percentage value will tend to lower the affinity between the blood slipping agent composition and menstrual blood, thus inhibiting it from sliding down into the interior of the absorbent article with menstrual blood that has reached the skin contact surface of the top sheet.

When the blood slipping agent-containing composition contains solid matter, it is preferably removed by filtration for measurement of the kinematic viscosity and water holding percentage.

The fibers composing such a woven fabric or nonwoven fabric as the liquid-permeable top sheet may be natural fibers or chemical fibers, with examples of natural fibers including cellulose, such as ground pulp and cotton, and examples of chemical fibers including regenerated cellulose, such as rayon and fibril rayon, semi-synthetic cellulose, such as acetate and triacetate, thermoplastic hydrophobic chemical fibers, and hydrophilicized thermoplastic hydrophobic chemical fibers.

Examples of thermoplastic hydrophobic chemical fibers include polyethylene (PE), polypropylene (PP) and polyethylene terephthalate (PET) monofilaments, and fibers including PE and PP graft polymers.

Examples of nonwoven fabrics include air-through nonwoven fabrics, spunbond nonwoven fabrics, point bond nonwoven fabrics, spunlace nonwoven fabrics, needle punching nonwoven fabrics and meltblown nonwoven fabrics, as well as combinations thereof (such as SMS and the like).

Liquid-impermeable back sheets include films comprising PE and PP, air-permeable resin films, air-permeable resin films bonded to spunbond or spunlace nonwoven fabrics, and multilayer nonwoven fabrics, such as SMS. In consideration of flexibility of the absorbent article, a low-density polyethylene (LDPE) film with a basis weight of about 15-30 g/m², for example, is preferred.

According to one embodiment of the absorbent article of the present disclosure, the absorbent article may comprise a second sheet between the liquid-permeable top sheet and the absorbent body. The second sheet may be any of the same examples as for the liquid-permeable top sheet.

The first example of the absorbent body is one having an absorbent core covered with a core wrap.

Examples of components for the absorbent core include hydrophilic fibers, including cellulose, such as ground pulp or cotton, regenerated cellulose, such as rayon or fibril rayon, semi-synthetic cellulose, such as acetate or triacetate, particulate polymers, filamentous polymers, thermoplastic hydrophobic chemical fibers, and hydrophilicized thermoplastic hydrophobic chemical fibers, as well as combinations of the foregoing. The component of the absorbent core may also be a super absorbent polymer, such as granules of a sodium acrylate copolymer or the like.

The core wrap is not particularly restricted so long as it is a substance that is liquid-permeable and with a barrier property that does not allow permeation of the polymer absorber, and it may be a woven fabric or nonwoven fabric, for example. The woven fabric or nonwoven fabric may be made of a natural fiber, chemical fiber, tissue, or the like.

A second example of the absorbent body is one formed from an absorbing sheet or polymer sheet, with a thickness of preferably about 0.3-5.0 mm. The absorbing sheet or polymer sheet may usually be used without any particular restrictions so long as it is one that can be used in an absorbent article, such as a sanitary napkin.

As regards the region in the planar direction wherein the liquid-permeable top sheet includes a blood slipping agent, according to one embodiment of the absorbent article of the present disclosure, the liquid-permeable top sheet comprises a blood slipping agent in the excretory opening contact region. According to another embodiment of the absorbent article of the present disclosure, the liquid-permeable top sheet also comprises a blood slipping agent in regions other than the excretory opening contact region, in addition to the excretory opening contact region, and for example, it may comprise the blood slipping agent across the entire surface of the top sheet.

As regards the region in the thickness direction in which the liquid-permeable top sheet includes a blood slipping agent, according to an embodiment of the absorbent article of the present disclosure, the liquid-permeable top sheet comprises a blood slipping agent on the surface of the skin side, i.e. on the skin contact surface. According to another embodiment of the absorbent article of the present disclosure, the liquid-permeable top sheet contains a blood slipping agent on the skin contact surface and in the interior between the skin contact surface and the clothing side surface. According to yet another embodiment of the absorbent article of the present disclosure, the liquid-permeable top sheet includes a blood slipping agent over the entire thickness direction, i.e. on the skin contact surface, in the interior between the skin contact surface and the clothing side surface, and on the clothing side surface. If the blood slipping agent is present in the top sheet interior and/or on the clothing side surface, menstrual blood present on the skin contact surface will rapidly migrate into the absorbent body.

The blood slipping agent preferably does not obstruct the voids between the fibers of the nonwoven fabric or woven fabric composing the top sheet, and for example, the blood slipping agent may be attached as droplets or particulates on the surface of the nonwoven fabric or woven fabric fibers, or covering the surfaces of the fibers.

In order for the blood slipping agent to migrate together with the absorbed menstrual blood, it preferably has a large surface area, and a blood slipping agent present as droplets or particulates preferably has a small droplet/particle size.

According to another embodiment of the absorbent article of the present disclosure, the absorbent article has a second sheet comprising a blood slipping agent or a blood slipping agent-containing composition. According to still another embodiment of the absorbent article of the present disclosure, the absorbent article has an absorbent body comprising a blood slipping agent or a blood slipping agent-containing composition.

When the nonwoven fabric or woven fabric coated with the blood slipping agent or blood slipping agent-containing composition is formed from a synthetic resin, the nonwoven fabric or woven fabric is preferably subjected to hydrophilicizing treatment. The hydrophilicizing treatment may involve coating the surfaces of the fibers of the nonwoven fabric or woven fabric with a hydrophilic agent, or mixing a hydrophilic agent with the synthetic resin used as the starting material for the nonwoven fabric or woven fabric.

This is because, if the material before coating of the blood slipping agent or blood slipping agent-containing composition is hydrophilic, there will be lipophilic regions due to the blood slipping agent, and hydrophilic regions due to the hydrophilic agent, that are sparsely dispersed on the top sheet, which will allow the blood slipping agent or blood slipping agent-containing composition to exhibit sliding performance and will facilitate rapid migration of menstrual blood into the absorbent body.

The blood slipping agent or blood slipping agent-containing composition may, if desired, be applied as a coating solution containing a volatile solvent, such as an alcohol-based solvent, ester-based solvent or aromatic solvent. If the coating solution includes a volatile solvent, the viscosity of the coating solution containing the blood slipping agent or blood slipping agent-containing composition will be lowered, thereby allowing the application steps to be simplified, facilitating application and making heating during application unnecessary.

There are no particular restrictions on the method of applying the blood slipping agent or blood slipping agent-containing composition, or the coating solution containing it, and if necessary the blood slipping agent or blood slipping agent-containing composition or the coating solution containing it may be heated, and a coating applicator, for example a non-contact coater, such as a spiral coater, curtain coater, spray coater or dip coater, or a contact coater, may be used for application of the blood slipping agent or blood slipping agent-containing composition or the coating solution containing it. The coating applicator is preferably a non-contact coater, from the viewpoint of uniformly dispersing the droplet or particulate modifying agent throughout, and from the viewpoint of not causing damage in the material.

The blood slipping agent or blood slipping agent-containing composition, or the coating solution containing it, may be coated directly, if it is a liquid at room temperature, or it may be heated to lower the viscosity, and when it is a solid at room temperature, it may be heated to liquefaction and coated from a control seam HMA (Hot Melt Adhesive) gun. By increasing the air pressure of the control seam HMA gun, it is possible to apply the blood slipping agent or blood slipping agent-containing composition as fine particulates.

The coating amount of the blood slipping agent or blood slipping agent-containing composition may be adjusted, for example, by reducing the amount of application from the control seam HMA gun.

There are also no particular restrictions on the method of forming an absorbent article having a top sheet wherein the basis weight of the blood slipping agent in the high fiber density region is greater than the basis weight of the blood slipping agent in the low fiber density region, and for example, (I) the number of control seam HMA guns may be increased, with a lower amount of blood slipping agent discharged from each gun, and the blood slipping agent or its composition applied around the high fiber density region as the centers, such as along the furrows, (II) a curtain coater may be used for application of the blood slipping agent or its composition with the high fiber density region as the centers, such as along the furrows, or (III) when the nonwoven fabric has a ridge-furrow structure, it may be dip coated with the furrow sides as the centers. Alternatively, (IV) heating may be carried out to lower the viscosity of the blood slipping agent, and the blood slipping agent may be coated onto the heated top sheet, the heated state being maintained thereafter, so that a fixed amount of the coated blood slipping agent migrates into the high fiber density region of the top sheet.

The blood slipping agent or its composition may be coated during production of the top sheet material, such as the nonwoven fabric, or it may be coated in the manufacturing line for production of the absorbent article. From the viewpoint of minimizing equipment investment, the blood slipping agent or its composition is preferably coated in the manufacturing line for the absorbent article, and in order to prevent shedding of the blood slipping agent which may contaminate the line, the blood slipping agent or its composition is preferably coated during a step downstream from the manufacturing line, and specifically, immediately before encapsulation of the product in an individual package.

The blood slipping agent also has an effect as a lubricant. Thus, the blood slipping agent reduces friction between the fibers, and can improve flexibility across the entire nonwoven fabric or woven fabric.

According to a preferred embodiment of the absorbent article of the present disclosure, the absorbent article is one that is intended for absorption of menstrual blood, such as a sanitary napkin or panty liner.

An absorbent article of the present disclosure does not require components, such as emollients and immobilizing agents, unlike in an absorbent article containing a known skin care composition, lotion composition or the like, and the blood slipping agent alone may be applied to the top sheet.

EXAMPLES

The present disclosure will now be explained in fuller detail by examples, with the understanding that it is not meant to be limited to the examples.

Example 1

There were prepared a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The top sheet used was produced according to the method described in Japanese Unexamined Patent Publication No. 2008-025084, and it was a top sheet having a ridge-furrow structure, with ridges as the low fiber density region and furrows as the high fiber density region. The top sheet had a ridge thickness of approximately 1.5 mm, a furrow thickness of approximately 0.4 mm, a ridge-furrow structure pitch (distance from the top part of one ridge to the top part of an adjacent ridge) of approximately 4 mm, and open holes in the furrows with an open area or approximately 15%.

PANACET 810s (product of NOF Corp., triester of glycerin and fatty acid) was selected as the blood slipping agent, and it was coated onto the skin contact surface (ridge-furrow side) of the top sheet from a control seam HMA gun at room temperature, to an average basis weight of 3 g/m$^2$, with the high fiber density region furrows as the centers.

A back sheet, an absorbent body, a second sheet, and a top sheet with the ridge-furrow side facing upward, were stacked in that order to form sanitary napkin No. 1-1.

Approximately 5 g each of a ridge and furrow were cut out from the top sheet that had been coated with the PANACET 810s, and the weights ($W_{R0}$ and $W_{G0}$, the former being the weight of the ridge and the latter being the weight of the furrow, units: g) and areas ($S_R$ and $S_G$, units: m$^2$) were precisely measured. Next the cut ridge and furrow were dipped in about 100 g of toluene at 25° C. for 5 minutes and then dried at 40° C. for 3 hours, and the dry weights ($W_{R1}$ and $W_{G1}$) were measured.

The basis weights of the blood slipping agent in the ridge and furrow were measured using the following formulas.

Basis weight of blood slipping agent in ridge (g/m$^2$)= [$W_{R0}$ (g)−$W_{R1}$ (g)]/$S_R$ (m$^2$)

Basis weight of blood slipping agent in furrow (g/m$^2$) = [$W_{G0}$ (g)−$W_{G1}$ (g)]/$S_G$ (m$^2$)

The basis weights of the blood slipping agent in the ridges and furrows were 1.96 g/m$^2$ and 3.22 g/m$^2$, respectively, indicating that the basis weight of the blood slipping agent in the furrows was 64% greater than the basis weight of the blood slipping agent in the ridges.

Next, sanitary napkin No. 1-2 was produced by the same method as the sanitary napkin No. 1-1, except that PANACET 810s was coated uniformly to a basis weight of 3 g/m$^2$.

When horse EDTA blood (horse blood to which ethylenediaminetetraacetic acid (hereunder, "EDTA") had been added to prevent coagulation) was dropped through a pipette onto the sanitary napkins No. 1-1 and 1-2, it was confirmed that sanitary napkin No. 1-1 blood was retained less easily at the high fiber density region furrows and migrated more rapidly into the absorbent body, compared to sanitary napkin No. 1-2.

The following experiment was also conducted in order to confirm the function of the blood slipping agent.

Example 2

Evaluation of Rewetting Rate and Absorbent Body Migration Rate

A commercially available sanitary napkin was prepared. The sanitary napkin was formed from a top sheet, formed of a hydrophilic agent-treated air-through nonwoven fabric (composite fiber composed of polyester and polyethylene terephthalate, basis weight: 35 g/m$^2$), a second sheet, formed of an air-through nonwoven fabric (composite fiber composed of polyester and polyethylene terephthalate, basis weight: 30 g/m$^2$), an absorbent body comprising pulp (basis weight: 150 to 450 g/m$^2$, increased at the center section), an acrylic super-absorbent polymer (basis weight: 15 g/m$^2$) and tissue as a core wrap, a water-repellent agent-treated side sheet, and a back sheet composed of a polyethylene film.

The blood slipping agents used for testing are listed below.

[($a_1$) Ester of a Chain Hydrocarbon Tetraols and at Least One Fatty Acid]

UNISTAR H-408BRS, product of NOF Corp.
Pentaerythritol tetra(2-ethylhexanoate), weight-average molecular weight: approximately 640
UNISTAR H-2408BRS-22, product of NOF Corp.
Mixture of pentaerythritol tetra(2-ethylhexanoate) and neopentylglycol di(2-ethylhexanoate) (58:42 as weight ratio), weight-average molecular weight: approximately 520

[($a_2$) Ester of a Chain Hydrocarbon Triols and at Least One Fatty Acid]

Cetiol SB45DEO, Cognis Japan
Glycerin and fatty acid triester, with oleic acid or stearylic acid as the fatty acid.
SOY42, product of NOF Corp.
Glycerin and fatty acid triester with C14 fatty acid:C16 fatty acid:C18 fatty acid:C20 fatty acid (including both saturated fatty acids and unsaturated fatty acids) at a mass ratio of about 0.2:11:88:0.8, weight-average molecular weight: 880.
Tri-C2L oil fatty acid glyceride, product of NOF Corp.
Glycerin and fatty acid triester with $C_8$ fatty acid:$C_{10}$ fatty acid:$C_{12}$ fatty acid at a mass ratio of about 37:7:56, weight-average molecular weight: approximately 570
Tri-CL oil fatty acid glyceride, product of NOF Corp.
Glycerin and fatty acid triester with $C_8$ fatty acid:$C_{12}$ fatty acid at a mass ratio of about 44:56, weight-average molecular weight: approximately 570
PANACET 810s, product of NOF Corp.
Glycerin and fatty acid triester with $C_8$ fatty acid:$C_{10}$ fatty acid at a mass ratio of about 85:15, weight-average molecular weight: approximately 480
PANACET 800, product of NOF Corp.
Glycerin and fatty acid triester with octanoic acid ($C_8$) as the entire fatty acid portion, weight-average molecular weight: approximately 470
PANACET 800B, product of NOF Corp.
Glycerin and fatty acid triester with 2-ethylhexanoic acid ($C_8$) as the entire fatty acid portion, weight-average molecular weight: approximately 470
NA36, product of NOF Corp.

Glycerin and fatty acid triester with $C_{16}$ fatty acid:$C_{18}$ fatty acid:$C_{20}$ fatty acid (including both saturated fatty acids and unsaturated fatty acids) at a mass ratio of about 5:92:3, weight-average molecular weight: approximately 880

Tri-coconut fatty acid glyceride, product of NOF Corp.

Glycerin and fatty acid triester with $C_8$ fatty acid:$C_{10}$ fatty acid:$C_{12}$ fatty acid:$C_{14}$ fatty acid:$C_{16}$ fatty acid (including both saturated fatty acids and unsaturated fatty acids) at a mass ratio of about 4:8:60:25:3, weight-average molecular weight: 670

Caprylic acid diglyceride, product of NOF Corp.

Glycerin and fatty acid diester with octanoic acid as the fatty acid, weight-average molecular weight: approximately 340

[($a_3$) Ester of a Chain Hydrocarbon Diol and at Least One Fatty Acid]

UNISTAR H-208BRS, product of NOF Corp.

Neopentyl glycol di(2-ethylhexanoate), weight-average molecular weight: approximately 360

COMPOL BL, product of NOF Corp.

Dodecanoic acid ($C_{12}$) monoester of butylene glycol, weight-average molecular weight: approximately 270

COMPOL BS, product of NOF Corp.

Octadecanoic acid ($C_{18}$) monoester of butylene glycol, weight-average molecular weight: approximately 350

[($c_2$) Ester of a Chain Hydrocarbon Tricarboxylic Acid, Hydroxy Acid, Alkoxy Acid or Oxoacid with 3 Carboxyl Groups, and at Least One Aliphatic Monohydric Alcohol]

Tributyl O-acetylcitrate, product of Tokyo Kasei Kogyo Co., Ltd.

Weight-average molecular weight: approximately 400

Tributyl citrate, product of Tokyo Kasei Kogyo Co., Ltd.

Weight-average molecular weight: approximately 360

[(c3) Ester of a Chain Hydrocarbon Dicarboxylic Acid, Hydroxy Acid, Alkoxy Acid or Oxoacid with 2 Carboxyl Groups, and at Least One Aliphatic Monohydric Alcohol]

Dioctyl adipate, product of Wako Pure Chemical Industries, Ltd.

Weight-average molecular weight: approximately 380

[($d_3$) Ester of a Fatty Acid and an Aliphatic Monohydric Alcohol]

ELECTOL WE20, product of NOF Corp.

Ester of dodecanoic acid ($C_{12}$) and dodecyl alcohol ($C_{12}$), weight-average molecular weight: approximately 360

ELECTOL WE40, product of NOF Corp.

Ester of tetradecanoic acid ($C_{14}$) and dodecyl alcohol ($C_{12}$), weight-average molecular weight: approximately 390

[($e_1$) Polyoxy $C_3$-$C_6$ alkylene glycol]

UNIOL PB500, product of NOF Corp.

Polybutylene glycol, weight-average molecular weight: approximately 500

UNIOL PB700, product of NOF Corp.

Polyoxybutylene polyoxypropylene glycol, weight-average molecular weight: approximately 700

[($f_1$) Chain Alkane]

PARLEAM 6, product of NOF Corp.

Branched chain hydrocarbon, produced by copolymerization of liquid isoparaffin, isobutene and n-butene followed by hydrogen addition, polymerization degree: approximately 5-10, weight-average molecular weight: approximately 330

[Other Materials]

NA50, product of NOF Corp.

Glycerin and fatty acid triester obtained by addition of hydrogen to NA36 for reduced proportion of double bonds from unsaturated fatty acid starting material, weight-average molecular weight: approximately 880

(Caprylic acid/capric acid) monoglyceride, product of NOF Corp.

Glycerin and fatty acid monoester, with octanoic acid ($C_8$) and decanoic acid ($C_{10}$) at a mass ratio of about 85:15, weight-average molecular weight: approximately 220

Monomuls 90-L2 lauric acid monoglyceride, product of Cognis Japan

Isopropyl citrate, product of Tokyo Kasei Kogyo Co., Ltd.

Weight-average molecular weight: approximately 230

Diisostearyl malate

Weight-average molecular weight: approximately 640

UNIOL PB1000R, product of NOF Corp.

Polybutylene glycol, weight-average molecular weight: approximately 1,000

UNIOL D-250, product of NOF Corp.

Polypropylene glycol, weight-average molecular weight: approximately 250

UNIOL D-400, product of NOF Corp.

Polypropylene glycol, weight-average molecular weight: approximately 400

UNIOL D-700, product of NOF Corp.

Polypropylene glycol, weight-average molecular weight: approximately 700

UNIOL D-1000, product of NOF Corp.

Polypropylene glycol, weight-average molecular weight: approximately 1,000

UNIOL D-1200, product of NOF Corp.

Polypropylene glycol, weight-average molecular weight: approximately 1,160

UNIOL D-2000, product of NOF Corp.

Polypropylene glycol, weight-average molecular weight: approximately 2,030

UNIOL D-3000, product of NOF Corp.

Polypropylene glycol, weight-average molecular weight: approximately 3,000

UNIOL D-4000, product of NOF Corp.

Polypropylene glycol, weight-average molecular weight: approximately 4,000

PEG1500, product of NOF Corp.

Polyethylene glycol, weight-average molecular weight: approximately 1,500-1,600

WILBRITE cp9, product of NOF Corp.

Polybutylene glycol compound with OH groups at both ends esterified by hexadecanoic acid ($C_{16}$), weight-average molecular weight: approximately 1,150

UNILUBE MS-70K, product of NOF Corp.

Stearyl ether of polypropylene glycol, approximately repeating units, weight-average molecular weight: approximately 1,140

NONION S-6, product of NOF Corp.

Polyoxyethylene monostearate, approximately 7 repeating units, weight-average molecular weight: approximately 880

UNILUBE 5TP-300 KB

Polyoxyethylene polyoxypropylene pentaerythritol ether, produced by addition of 5 mol of ethylene oxide and 65 mol of propylene oxide to 1 mol of pentaerythritol, weight-average molecular weight: 4,130

WILBRITE s753, product of NOF Corp.

Polyoxyethylene polyoxypropylene polyoxybutylene glycerin, weight-average molecular weight: approximately 960

UNIOL TG-330, product of NOF Corp.

Glyceryl ether of polypropylene glycol, approximately 6 repeating units, weight-average molecular weight: approximately 330

UNIOL TG-1000, product of NOF Corp.
Glyceryl ether of polypropylene glycol, approximately 16 repeating units, weight-average molecular weight: approximately 1,000

UNIOL TG-3000, product of NOF Corp.
Glyceryl ether of polypropylene glycol, approximately 16 repeating units, weight-average molecular weight: approximately 3,000

UNIOL TG-4000, product of NOF Corp.
Glyceryl ether of polypropylene glycol, approximately 16 repeating units, weight-average molecular weight: approximately 4,000

UNILUBE DGP-700, product of NOF Corp.
Diglyceryl ether of polypropylene glycol, approximately 9 repeating units, weight-average molecular weight: approximately 700

UNIOX HC60, product of NOF Corp.
Polyoxyethylene hydrogenated castor oil, weight-average molecular weight: approximately 3,570

Vaseline, product of Cognis Japan
Petroleum-derived hydrocarbon, semi-solid

The kinematic viscosities, water holding percentages, weight-average molecular weights, IOBs and melting points of the samples are shown in Table 2.

For the melting point, "<45" indicates a melting point of below 45° C.

Almost the entire skin contact surface of the top sheet of the sanitary napkin was coated with the aforementioned blood slipping agent. Each blood slipping agent was used directly, when it was liquid at room temperature, or when the blood slipping agent was solid at room temperature it was heated to its melting point of +20° C., and then a control seam HMA gun was used for atomization of each blood slipping agent and coating onto the skin contact surface of the top sheet to a basis weight of about 5 g/m$^2$.

Figure 6:
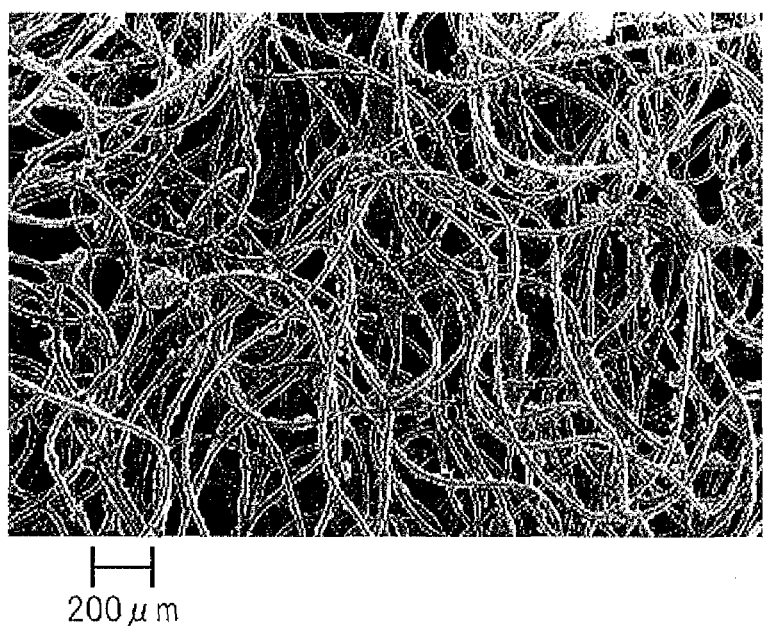
FIG. 6 is an electron micrograph of the skin contact surface of a top sheet in a sanitary napkin wherein the top sheet comprises tri-C2L oil fatty acid glycerides.

FIG. 6 is an electron micrograph of the skin contact surface of a top sheet in a sanitary napkin (No. 2-5) wherein the top sheet comprises tri-C2L oil fatty acid glycerides. As clearly seen in FIG. 6, the tri-C2L oil fatty acid glycerides are present on the fiber surfaces as fine particulates.

[Test Methods]

An acrylic board with an opened hole (200 mm×100 mm, 125 g, with a 40 mm×10 mm hole opened at the center) was placed on a top sheet comprising each blood slipping agent, and 3 g of horse EDTA blood at 37±1° C. was dropped through the hole using a pipette (once), and after 1 minute, 3 g of horse EDTA blood at 37±1° C. was again added dropwise through the acrylic board hole with a pipette (twice).

After the second dropping of blood, the acrylic board was immediately removed and 10 sheets of filter paper (Qualitative filter paper No. 2, product of Advantech Toyo, Inc., 50 mm×35 mm) (total weight of 10 filter sheets: $FW_0$ (g)) were placed on the location where the blood had been dropped, and then a weight was placed thereover at a pressure of 30 g/cm$^2$. After 1 minute, the filter paper was removed, the total weight $FW_1$ (g) of the 10 tested filter sheets was measured, and the "rewetting rate" was calculated by the following formula.

$$\text{Rewetting rate(mass \%)} = 100 \times [FW_1 (g) - FW_0 (g)]/6.0 (g)$$

In addition to the rewetting rate evaluation, the "absorbent body migration rate" was also measured as the time until migration of blood from the top sheet to the absorbent body after the second dropping of blood. The absorbent body migration rate is the time from introducing the blood onto the top sheet, until the redness of the blood could be seen on the surface and in the interior of the top sheet.

The results for the rewetting rate and absorbent body migration rate are shown below in Table 2.

The whiteness of the skin contact surface of the top sheet (TS) after the absorbent body migration rate test was visually evaluated on the following scale.

VG (Very Good): Virtually no redness of blood remaining, and no clear delineation between areas with and without blood.

G (Good): Slight redness of blood remaining, but difficult to delineate between areas with and without blood.

F (Fair): Slight redness of blood remaining, areas with blood discernible.

P (Poor): Redness of blood completely remaining.

The tack on the skin contact surface of the top sheet was also measured at 35° C., and evaluated on the following scale.

G: No tack
F: Slight tack
P: Tack

The results are summarized in Table 2 below.

TABLE 2

| No. | Blood lubricity imparter | Kinematic viscosity (mm$^2$/s, 40° C.) | Water holding percentage (mass %) | Weight-average mol. wt. | IOB | Melting pt. (° C.) | Rewetting rate (%) | Absorbent body migration rate (sec) | TS whiteness | Tack |
|---|---|---|---|---|---|---|---|---|---|---|
| 2-1 | H-408BRS | 45 | 0.7 | 640 | 0.13 | <−5 | 1.2 | 3 | VG | G |
| 2-2 | H-2408BRS-22 | 22 | 0.8 | 520 | 0.18 | <−5 | 2.0 | 3 | VG | G |
| 2-3 | Cetiol SB45DEO | | | | 0.16 | 44 | 7.0 | 6 | VG | |
| 2-4 | SOY42 | | | 880 | 0.16 | 43 | 5.8 | 8 | VG | G |
| 2-5 | Tri-C2L oil fatty acid glycerides | 20 | <1.0 | 570 | 0.27 | 37 | 0.3 | 3 | VG | G |
| 2-6 | Tri-CL oil fatty acid glycerides | 15 | <1.0 | 570 | 0.28 | 38 | 1.7 | 3 | VG | G |
| 2-7 | PANACET 810s | 9 | 0.3 | 480 | 0.32 | −5 | 2.8 | 3 | VG | G |
| 2-8 | PANACET 800 | 15 | 0.5 | 470 | 0.33 | −5 | 0.3 | 3 | VG | G |
| 2-9 | PANACET 800B | 20 | <1.0 | 470 | 0.33 | −5 | 2.0 | 3 | VG | G |
| 2-10 | NA36 | 40 | <1.0 | 880 | 0.16 | 37 | 3.9 | 5 | VG | G |
| 2-11 | Tri-coconut oil fatty acid glycerides | 25 | <1.0 | 670 | 0.28 | 30 | 4.3 | 5 | VG | G |
| 2-12 | Caprylic acid diglyceride | 25 | 2.7 | 340 | 0.58 | <45 | 4.2 | 9 | G | G |

TABLE 2-continued

| No. | Blood lubricity imparter | Kinematic viscosity (mm²/s, 40° C.) | Water holding percentage (mass %) | Weight-average mol. wt. | IOB | Melting pt. (° C.) | Rewetting rate (%) | Absorbent body migration rate (sec) | TS whiteness | Tack |
|---|---|---|---|---|---|---|---|---|---|---|
| 2-13 | UNISTAR H-208BRS | 8 | 0.7 | 360 | 0.24 | <−5 | 2.0 | 5 | VG | G |
| 2-14 | COMPOL BL | 10 | 1.6 | 270 | 0.50 | 2 | 2.0 | 5 | G | G |
| 2-15 | COMPOL BS | 35 | 0.3 | 350 | 0.36 | 37 | 7.9 | 9 | G | G |
| 2-16 | Tributyl O-acetylcitrate | 15 | 0.9 | 400 | 0.60 | <45 | 6.2 | 8 | VG | G |
| 2-17 | Tributyl citrate | 12 | 0.6 | 360 | 0.78 | <45 | 3.0 | 6 | G | G |
| 2-18 | Dioctyl adipate | 7 | 0.4 | 380 | 0.27 | <45 | 1.7 | 6 | VG | G |
| 2-19 | ELECTOL WE20 | 10 | 0.3 | 360 | 0.13 | 29 | 1.8 | 5 | VG | G |
| 2-20 | ELECTOL WE40 | 15 | 0.5 | 390 | 0.12 | 37 | 1.8 | 4 | VG | G |
| 2-21 | UNIOL PB500 | 40 | 3.6 | 500 | 0.44 | <45 | 4.5 | 4 | G | G |
| 2-22 | UNIOL PB700 | 50 | 2.3 | 700 | 0.49 | −5 | 2.8 | 5 | G | G |
| 2-23 | PARLEAM 6 | 5 | 0.06 | 330 | 0.00 | −5 | 6.0 | 8 | VG | G |
| 2-24 | NA50 | 80<< | —* | 880 | 0.18 | 52 | 15.5 | 60 | P | G |
| 2-25 | (Caprylic acid/Capric acid) monoglyceride | 70 | 4.0<< | 220 | 1.15 | <45 | 4.0 | 4 | P | G |
| 2-26 | 90-L2 Lauric acid monoglyceride | 80<< | 4.0<< | <1,000 | 0.87 | 58 | 6.2 | 7 | P | G |
| 2-27 | Isopropyl citrate | 120 | 4.0<< | 230 | 1.56 | <45 | 12.2 | 5 | G | F |
| 2-28 | Diisostearyl malate | 450 | 4.0<< | 640 | 0.28 | <45 | 5.5 | 8 | F | F |
| 2-29 | UNIOL PB1000R | 70 | 5.5 | 1000 | 0.40 | <45 | 4.0 | 4 | G | F |
| 2-30 | UNIOL D-250 | 20 | 4.0<< | 250 |  | <45 | — | — | P | G |
| 2-31 | UNIOL D-400 | 30 | 4.0<< | 400 | 0.76 | <45 | 8.7 | 40 | P | G |
| 2-32 | UNIOL D-700 | 50 | 34.6 | 700 | 0.58 | <45 | 7.5 | — | F | G |
| 2-33 | UNIOL D-1000 | 70 | 26.7 | 1,000 | 0.51 | <45 | 6.8 | 15 | F | F |
| 2-34 | UNIOL D-1200 | 90 | 16.2 | 1,160 | 0.48 | <45 | 0.5 | 11 | F | F |
| 2-35 | UNIOL D-2000 | 160 |  | 2,030 |  | <45 | — | — | F | P |
| 2-36 | UNIOL D-3000 |  | 0.6 | 3,000 | 0.39 | <45 | 1.7 | 10 | F | P |
| 2-37 | UNIOL D-4000 | 450 | 0.5 | 4,000 | 0.38 | <45 | 1.0 | 7 | G | P |
| 2-38 | PEG1500 | 120 | 4.0<< | 1,500-1,600 | 0.78 | 40 | 11.0 | 38 | P | P |
| 2-39 | WILBRITE CP9 | 120 | 0.6 | 1,150 | 0.21 | 35 | 1.4 | 3 | G | P |
| 2-40 | UNILUBE MS-70K | 50 | 2.8 | 1,140 | 0.30 | <−10 | 6.7 | 3 | G | F |
| 2-41 | NONION S-6 | 65 | 4.0<< | 880 | 0.44 | 37 | 8.4 | 7 | P | G |
| 2-42 | UNILUBE 5TP-300KB | 310 | 3.9 | 4,130 | 0.39 | <45 | 2.0 | 6 | G | P |
| 2-43 | WILBRITE s753 | 120 | 27.3 | 960 | 0.67 | −5 | 9.3 | 9 | F | F |
| 2-44 | UNIOL TG-330 | 30 |  | 330 | 1.27 | <45 | — | — | — | G |
| 2-45 | UNIOL TG-1000 | 100 | 21.2 | 1,000 | 0.61 | <45 | 14.2 | 7 | G | G |
| 2-46 | UNIOL TG-3000 | 230 | 4.3 | 3,000 | 0.42 | <45 | 0.8 | 6 | G | P |
| 2-47 | UNIOL TG-4000 | 300 | 2.4 | 4,000 | 0.40 | <45 | 2.0 | 6 | G | P |
| 2-48 | UNILUBE DGP-700 | 200 | 4.0<< | 700 | 0.91 | <0 | 8.0 | 10 | F | F |
| 2-49 | UNIOX HC60 | 1150 |  | 3,570 | 0.46 | 33 | 14.6 | 46 | P | P |
| 2-50 | Vaseline | 80<< | 0.0 | <1,000 | 0.00 | 55 | 9.7 | 10 | F | P |
| 2-51 | None | — | — | — | — | — | 22.7 | 60< | P | G |

*Viscosity too high for measurement.

In the absence of a blood slipping agent, the rewetting rate was 22.7% and the absorbent body migration rate was greater than 60 seconds, but the glycerin and fatty acid triesters all produced rewetting rates of 7.0% or less and absorbent body migration rates of no longer than 8 seconds, and therefore significantly improved the absorption performance.

Similarly, it was found that the absorption performance is greatly improved with a blood slipping agent having a kinematic viscosity of about 0.01 to 80 mm²/s at 40° C., a water holding percentage of about 0.01 to about 4.0 mass %, and a weight-average molecular weight of less than about 1000.

Next, several volunteer subjects were asked to wear sanitary napkins Nos. 2-1 to 2-51, and the obtained responses indicated that with the sanitary napkins comprising blood slipping agent Nos. 2-1 to 2-23, the top sheets had no sticky feel and the top sheets were smooth, even after absorption of menstrual blood.

Also, with sanitary napkins that comprised blood slipping agent Nos. 2-11, 13, 16, 18-20 and 23, the skin contact surfaces of the top sheets after absorption of menstrual blood had not been reddened by the menstrual blood and the unpleasantness was minimal.

Example 3

Surface Residue Rate of Menstrual Blood on Top Sheet with Ridge-Furrow Structure The surface residue rate of menstrual blood on a top sheet with a ridge-furrow structure was evaluated.

There were prepared a top sheet, formed of a hydrophilic agent-treated air-through nonwoven fabric (composite fiber composed of polyester and polyethylene terephthalate, basis weight: 35 g/m²), a second sheet, formed of an air-through nonwoven fabric (composite fiber composed of polyester and polyethylene terephthalate, basis weight: 30 g/m²), an absorbent body comprising pulp (basis weight: 150 to 450 g/m², increased at the center section), an acrylic super-absorbent polymer (basis weight: 15 g/m²) and tissue as a core wrap, a water-repellent agent-treated side sheet, and a back sheet composed of a polyethylene film.

The top sheet used was produced according to the method described in Japanese Unexamined Patent Publication No. 2008-025084, and it was a top sheet having a ridge-furrow structure, with ridges as the high fiber density region and furrows as the low fiber density region. The top sheet had a ridge thickness of approximately 1.5 mm, a furrow thickness of approximately 0.4 mm, a ridge-furrow structure pitch (distance from the top part of one ridge to the top part of an adjacent ridge) of approximately 4 mm, and open holes in the furrows with an open area or approximately 15%.

UNISTAR H-408BRS (product of NOF Corp., tetraester of pentaerythritol and fatty acid) was selected as the blood slipping agent, and it was coated onto the skin contact surface (ridge-furrow side) of the top sheet from a control seam HMA gun at room temperature, to a basis weight of 5.0 g/m². With an electron microscope it was confirmed that the H-408BRS was adhering onto the fiber surfaces as fine particulates.

A back sheet, an absorbent body, a second sheet, and a top sheet with the ridge-furrow side facing upward, were stacked in that order to form sanitary napkin No. 3-1.

Sanitary napkins No. 3-2 to No. 3-40 were produced, changing the blood slipping agent from UNISTAR H-408BRS to the ones listed in Table 3. Each blood slipping agent was used directly, when it was liquid at room temperature, or when the blood slipping agent was solid at room temperature it was heated to its melting point of +20° C., and then a control seam HMA gun was used for atomization of the blood slipping agent and coating onto the skin contact surface of the top sheet to a basis weight of about 5 g/m².

The blood slipping agent was coated onto essentially the entire skin contact surface of the top sheet, and on both the ridges and furrows.

[Test Methods]

After measuring the mass: $W_2$ (g) of the top sheet (the mass of the top sheet before the test), an acrylic board with an opened hole (200 mm×100 mm, 125 g, with a 40 mm×10 mm hole opened at the center) was placed on the top sheet, at the center section in the lengthwise direction and widthwise direction of the absorbent article, and 4.0 g of horse EDTA blood at 37±1° C. (obtained by adding ethylenediaminetetraacetic acid (hereunder, "EDTA") to horse blood to prevent coagulation) was dropped through the hole using a pipette.

After dropping the horse EDTA blood, the acrylic board was immediately removed, the top sheet was taken off, the mass $W_3$ (g) (mass of top sheet after the test) was measured and the "surface residue rate (mass %)" was calculated by the following formula.

Surface residue rate (mass %)=100×[$W_3$ (g)−$W_2$ (g)]/ 4.0 (g)

The results are summarized in Table 3 below.

TABLE 3

| No. | Blood slipping agent | Surface residue rate (mass %) |
|---|---|---|
| 3-1 | H-408BRS | 0.8 |
| 3-2 | H-2408BRS-22 | 0.8 |
| 3-3 | PANACET 810s | 0.8 |
| 3-4 | PANACET 800 | 1.8 |
| 3-5 | Caprylic acid diglyceride | 1.0 |
| 3-6 | UNISTAR H-208BRS | 0.5 |
| 3-7 | COMPOL BL | 1.3 |
| 3-8 | COMPOL BS | 2.5 |
| 3-9 | Tributyl O-acetylcitrate | 0.5 |
| 3-10 | Tributyl citrate | 1.8 |
| 3-11 | Dioctyl adipate | 1.5 |
| 3-12 | ELECTOL WE20 | 0.5 |
| 3-13 | ELECTOL WE40 | 2.3 |
| 3-14 | UNIOL PB500 | 2.5 |
| 3-15 | UNIOL PB700 | 1.3 |
| 3-16 | PARLEAM 6 | 2.0 |
| 3-17 | NA50 | 4.3 |
| 3-18 | (Caprylic acid/capric acid) monoglyceride | 5.0 |
| 3-19 | 90-L2 Lauric acid monoglyceride | 5.0 |
| 3-20 | Isopropyl citrate | 4.8 |
| 3-21 | Diisostearyl malate | 3.3 |

TABLE 3-continued

| No. | Blood slipping agent | Surface residue rate (mass %) |
|---|---|---|
| 3-22 | UNIOL PB1000R | 2.5 |
| 3-23 | UNIOL D-250 | 3.8 |
| 3-24 | UNIOL D-400 | 4.8 |
| 3-25 | UNIOL D-700 | 4.8 |
| 3-26 | UNIOL D-1000 | 3.8 |
| 3-27 | UNIOL D-1200 | 3.0 |
| 3-28 | UNIOL D-3000 | 3.0 |
| 3-29 | UNIOL D-4000 | 2.5 |
| 3-30 | PEG1500 | 5.5 |
| 3-31 | WILBRITE CP9 | 6.8 |
| 3-32 | UNILUBE MS-70K | 1.5 |
| 3-33 | UNILUBE 5TP-300KB | 2.0 |
| 3-34 | WILBRITE s753 | 3.5 |
| 3-35 | UNIOL TG-1000 | 3.5 |
| 3-36 | UNIOL TG-3000 | 1.0 |
| 3-37 | UNIOL TG-4000 | 2.0 |
| 3-38 | UNILUBE DGP-700 | 3.5 |
| 3-39 | Vaseline | 4.0 |
| 3-40 | None | 7.5 |

With sanitary napkin No. 3-40, which had no blood slipping agent, the surface residue rate was 7.5 mass %, but with sanitary napkins No. 3-1 to No. 3-16 wherein the kinematic viscosity and water holding percentage were within the prescribed ranges, the surface residue rate was 2.5 mass % or lower.

With sanitary napkins No. 3-1 to No. 3-16, it was observed that the horse EDTA blood that was dropped onto the ridges of the top sheet slipped down from the ridges into the furrows, and was rapidly absorbed from the furrows into the absorbent body. However, with sanitary napkin No. 3-40 which had no blood slipping agent, the dropped horse EDTA blood did not slip down into the furrows but slowly dripped down into the furrows, most of it remaining on the ridges of the top sheet. Also, with the absorbent articles with high water holding percentage, as with No. 3-25, for example, the horse EDTA blood that was dropped onto the ridges of the top sheet did not slip down into the furrows but slowly dripped while partially remaining on the top sheet, and a portion thereof remained on the ridges.

Examples 2 and 3 are not examples where the top sheet has a higher basis weight of the blood slipping agent in the high fiber density region than the basis weight of the blood slipping agent in the low fiber density region within the excretory opening contact region, but they confirmed that a prescribed amount of blood slipping agent allows menstrual blood to slide down and migrate into the absorbent body. It is clear, therefore, that an absorbent article according to the present disclosure, wherein the basis weight of the blood slipping agent in the high fiber density region is greater than the basis weight of the blood slipping agent in the low fiber density region, minimizes retention of absorbed menstrual blood in the high fiber density region and thus helps prevent a sticky feel in the top sheet after menstrual blood has been absorbed.

Example 4

Viscosity of Blood Containing Blood Slipping Agent

The viscosity of the blood slipping agent-containing blood was measured using a Rheometric Expansion System ARES (Rheometric Scientific, Inc.). After adding 2 mass % of PANACET 810s to horse defibrinated blood, the mixture was gently agitated to form a sample, the sample was placed on a 50 mm-diameter parallel plate, with a gap of 100 μm, and the viscosity was measured at 37±0.5° C. The sample was not subjected to a uniform shear rate due to the parallel plate, but the average shear rate indicated by the device was 10 s$^{-1}$.

The viscosity of the horse defibrinated blood containing 2 mass % PANACET 810s was 5.9 mPa·s, while the viscosity of the horse defibrinated blood containing no blood slipping agent was 50.4 mPa·s. Thus, the horse defibrinated blood containing 2 mass % PANACET 810s clearly had an approximately 90% lower viscosity than the blood containing no blood slipping agent.

It is known that blood contains components, such as blood cells and has a thixotropic nature, and the blood slipping agent of the present disclosure has an effect of lowering the viscosity of blood, such as menstrual blood in the low viscosity range. Lowering the blood viscosity allows absorbed menstrual blood to more easily migrate rapidly from the top sheet to the absorbent body.

Example 5

Photomicrograph of Blood Slipping Agent-Containing Menstrual Blood

Menstrual blood was sampled from healthy volunteers onto thin plastic wrap, and PANACET 810s dispersed in a 10-fold mass of phosphate-buffered saline was added to a portion thereof to a PANACET 810s concentration of 1 mass %. The menstrual blood was dropped onto a slide glass, a cover glass was placed thereover, and the state of the erythrocytes was observed with an optical microscope. A photomicrograph of menstrual blood containing no blood slipping agent is shown in FIG. 7(a), and a photomicrograph of menstrual blood containing PANACET 810s is shown in FIG. 7(b).

Figure 7:
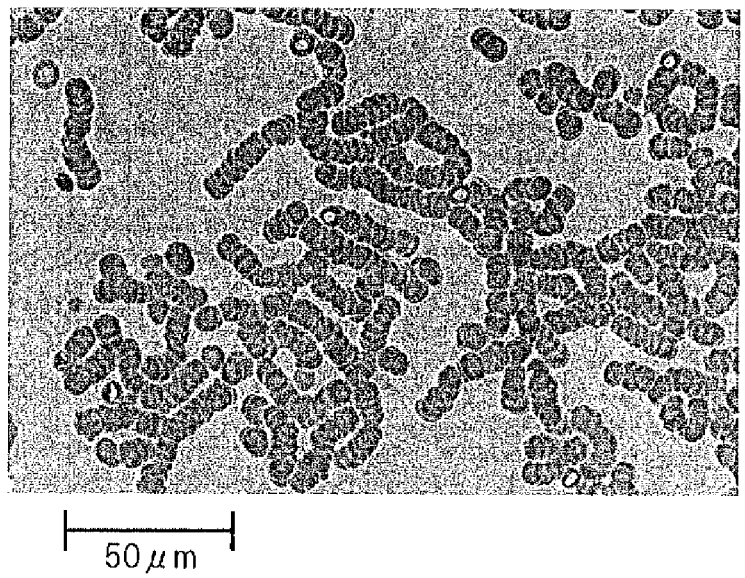
FIG. 7 is a pair of photomicrographs of menstrual blood containing and not containing a blood slipping agent.
Figure 7:
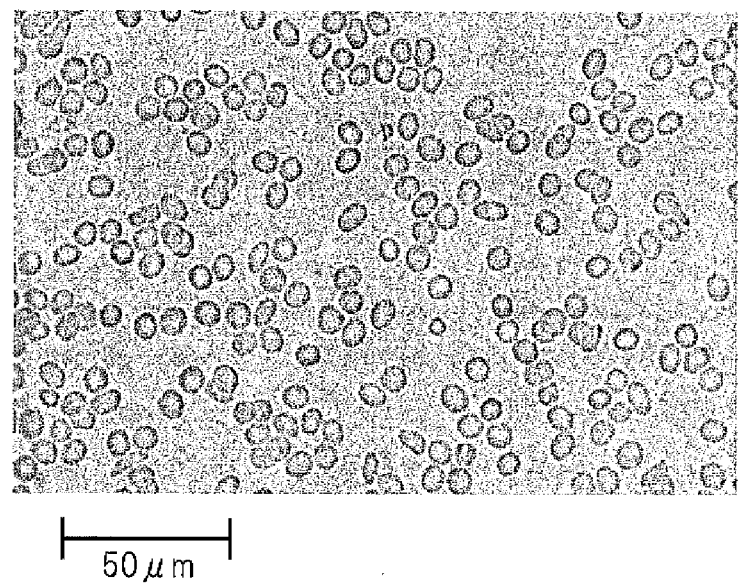

FIG. 7(a) shows that the erythrocytes formed aggregates, including a rouleaux structure, in the menstrual blood containing no blood slipping agent, while FIG. 7(b) shows that the erythrocytes were stably dispersed in the menstrual blood containing PANACET 810s. This suggests that the blood slipping agent has the function of stabilizing erythrocytes in menstrual blood.

Example 6

Surface Tension of Blood Containing Blood Slipping Agent

The surface tension of blood containing a blood slipping agent was measured by the pendant drop method, using a Drop Master500 contact angle meter by Kyowa Interface Science Co., Ltd. The surface tension was measured after adding a prescribed amount of blood slipping agent to sheep defibrinated blood, and thoroughly shaking.

Figure 8:
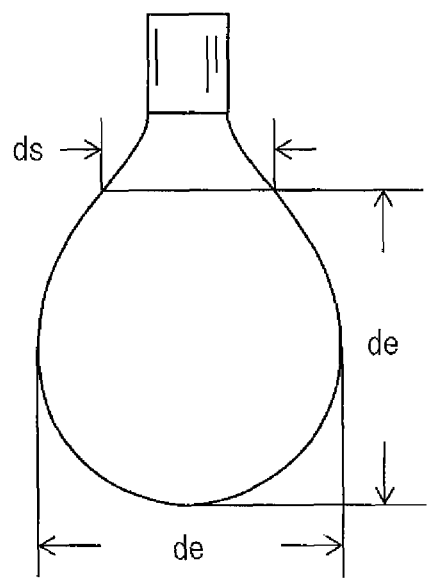
FIG. 8 is a diagram illustrating a method of measuring surface tension.

The measurement was accomplished automatically with a device, and the surface tension γ was determined by the following formula (see FIG. 8).

$$\gamma = g \times \rho \times (de)^2 \times 1/H$$

g: Gravitational constant
1/H: Correction factor determined from ds/de
ρ: Density
de: Maximum diameter
ds: Diameter at location of increase by de from dropping edge The density ρ was measured at the temperatures listed in Table 4, according to JIS K 2249-1995, "Density test methods and density/mass/volume conversion tables", "5. Vibrating density test method".

The measurement was accomplished using a DA-505 by Kyoto Electronics Co., Ltd.

The results are shown in Table 4 below.

TABLE 4

| No. | Blood slipping agent Type | Amount (mass %) | Measuring temperature (°C.) | Surface tension (mN/m) |
|---|---|---|---|---|
| 4-1 | — | — | 35 | 62.1 |
| 4-2 | PANACET | 0.01 | 35 | 61.5 |
| 4-3 | 810s | 0.05 | 35 | 58.2 |
| 4-4 |  | 0.10 | 35 | 51.2 |
| 4-5 | ELECTOL WE20 | 0.10 | 35 | 58.8 |
| 4-6 | PARLEAM 6 | 0.10 | 35 | 57.5 |
| 4-7 | — | — | 50 | 56.3 |
| 4-8 | WILBRITE cp9 | 0.10 | 50 | 49.1 |

Based on Table 4 it is seen that the blood slipping agent has an effect of lowering the surface tension of blood.

Lowering the surface tension of blood allows absorbed blood to rapidly migrate from the top sheet to the absorbent body, without being retained between the top sheet fibers.

The present disclosure relates to the following J1 to J15.

[J1]

An absorbent article comprising a liquid-permeable top sheet, a liquid-impermeable back sheet, and an absorbent body between the top sheet and the back sheet, wherein the top sheet is formed from a nonwoven fabric or woven fabric having in the excretory opening contact region, a high fiber density region, and a low fiber density region with lower fiber density than the high fiber density region, the top sheet comprises in the excretory opening contact region, a blood slipping agent with a kinematic viscosity of 0.01 to 80 mm$^2$/s at 40° C., a water holding percentage of 0.01 to 4.0 mass % and a weight-average molecular weight of less than 1000, and the basis weight of the blood slipping agent in the high fiber density region is higher than the basis weight of the blood slipping agent in the low fiber density region.

[J2]

The absorbent article according to J1, wherein the blood slipping agent further has an IOB of 0.00-0.60.

[J3]

The absorbent article according to J1 or J2, wherein the top sheet has a ridge-furrow structure with a plurality of ridges and a plurality of furrows, the ridges are a high sheet basis weight region with a higher sheet basis weight than the average sheet basis weight of the top sheet, and the furrows are a low sheet basis weight region with a lower sheet basis weight than the average sheet basis weight of the top sheet.

[J4]

The absorbent article according to any one of J1 to J3, wherein the ridges are the low fiber density region and the furrows are the high fiber density region.

[J5]

The absorbent article according to any one of J1 to J3, wherein the ridges are the high fiber density region and the furrows are the low fiber density region.

[J6]

The absorbent article according to J4 or J5, wherein the top sheet has one or more open holes in the furrows.

[J7]

The absorbent article according to any one of J1 to J6, wherein the basis weight of the blood slipping agent in the high fiber density region is 1 to 30 g/m².

[J8]

The absorbent article according to any one of J1 to J7, wherein the basis weight of the blood slipping agent in the high fiber density region is 3-90% higher than the basis weight of the blood slipping agent in the low fiber density region.

[J9]

The absorbent article according to any one of J1 to J8, wherein the blood slipping agent is selected from the group consisting of following items (i)-(iii), and any combination thereof:

(i) a hydrocarbon;

(ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety;

with the proviso that when 2 or more oxy groups are inserted in the compound of (ii) or (iii), the oxy groups are not adjacent.

[J10]

The absorbent article according to any one of J1 to J9, wherein the blood slipping agent is selected from the group consisting of following items (i')-(iii'), and any combination thereof:

(i') a hydrocarbon;

(ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety;

with the proviso that when 2 or more same or different bonds are inserted in a compound of (ii') or (iii'), the bonds are not adjacent.

[J11]

The absorbent article according to any one of J1 to J10, wherein the blood slipping agent is selected from the group consisting of following items (A)-(F), and any combination thereof:

(A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;

(B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;

(C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;

(D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;

(E) a polyoxy $C_3$-$C_6$ alkylene glycol, or alkyl ester or alkyl ether thereof; and (F) a chain hydrocarbon.

[J12]

The absorbent article according to any one of J1 to J11, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycols and at least one fatty acid, ($e_3$) an ether of a polyoxy $C_3$-$C_6$ alkylene glycol and at least one aliphatic monohydric alcohol, and ($f_1$) a chain alkane, and any combination thereof.

[J13]

The absorbent article according to any one of J1 to J12, wherein in the excretory opening contact region, the blood slipping agent is attached to the surfaces of the fibers of the nonwoven fabric or woven fabric as droplets or particulates.

[J14]

The absorbent article according to any one of J1 to J13, wherein the top sheet has been subjected to hydrophilicizing treatment.

[J15]

An absorbent article according to any one of J1 to J14, wherein the absorbent article is a sanitary napkin or panty liner.

REFERENCES SIGNS LIST

1 Sanitary napkin
2 Top sheet
3 Absorbent body
4 Side sheet
5 Embossed section

6 Back sheet
7 High fiber density region
8 Low fiber density region
9,9' blood slipping agents
10 Ridge
11 Furrow
12 Open hole

The invention claimed is:

1. An absorbent article comprising a liquid-permeable top sheet, a liquid-impermeable back sheet, and an absorbent body between the top sheet and the back sheet,
   wherein the top sheet is formed from a nonwoven fabric or woven fabric having in the excretory opening contact region, a high fiber density region, and a low fiber density region with lower fiber density than the high fiber density region,
   the top sheet comprises in the excretory opening contact region, a blood slipping agent with a kinematic viscosity of 0.01 to 80 mm$^2$/s at 40° C., a water holding percentage of 0.01 to 4.0 mass % and a weight-average molecular weight of less than 1000, and
   the basis weight of the blood slipping agent in the high fiber density region is higher than the basis weight of the blood slipping agent in the low fiber density region, wherein the basis weight of the blood slipping agent in the high fiber density region is 1 to 30 g/m$^2$.

2. The absorbent article according to claim 1, wherein the blood slipping agent further has an IOB of 0.00-0.60.

3. The absorbent article according to claim 1, wherein the top sheet has a ridge-furrow structure with a plurality of ridges and a plurality of furrows, the ridges of the plurality of ridges are a high sheet basis weight region with a higher sheet basis weight than the average sheet basis weight of the top sheet, and the furrows of the plurality of furrows are a low sheet basis weight region with a lower sheet basis weight than the average sheet basis weight of the top sheet.

4. The absorbent article according to claim 1, wherein the ridges of the plurality of ridges are the low fiber density region and the furrows of the plurality of furrows are the high fiber density region.

5. The absorbent article according to claim 4, wherein the top sheet has one or more open holes in the furrows of the plurality of furrows.

6. The absorbent article according to claim 1, wherein the ridges of the plurality of ridges are the high fiber density region and the furrows of the plurality of furrows are the low fiber density region.

7. The absorbent article according to claim 1, wherein the basis weight of the blood slipping agent in the high fiber density region is 3-90% higher than the basis weight of the blood slipping agent in the low fiber density region.

8. The absorbent article according to claim 1, wherein the blood slipping agent is selected from the group consisting of following items (i)-(iii), and any combination thereof:
   a hydrocarbon;
   (ii) a compound having (ii-1) a hydrocarbon moiety, and (ii-2) one or more, same or different groups selected from the group consisting of carbonyl group (—CO—) and oxy group (—O—) inserted between a C—C single bond of the hydrocarbon moiety; and
   (iii) a compound having (iii-1) a hydrocarbon moiety, (iii-2) one or more, same or different groups selected from the group consisting of carbonyl group (—CO—) and oxy group (—O—) inserted between a C—C single bond of the hydrocarbon moiety, and (iii-3) one or more, same or different groups selected from the group consisting of carboxyl group (—COOH) and hydroxyl group (—OH) substituting for a hydrogen of the hydrocarbon moiety;
   with the proviso that when 2 or more oxy groups are inserted in the compound of (ii) or (iii), the oxy groups are not adjacent.

9. The absorbent article according to claim 1, wherein the blood slipping agent is selected from the group consisting of following items (i')-(iii'), and any combination thereof:
   (i') a hydrocarbon;
   (ii') a compound having (ii'-1) a hydrocarbon moiety, and (ii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety; and
   (iii') a compound having (iii'-1) a hydrocarbon moiety, (iii'-2) one or more, same or different bonds selected from the group consisting of carbonyl bond (—CO—), ester bond (—COO—), carbonate bond (—OCOO—), and ether bond (—O—) inserted between a C—C single bond of the hydrocarbon moiety, and (iii'-3) one or more, same or different groups selected from the group consisting of carboxyl group (—COOH) and hydroxyl group (—OH) substituting for a hydrogen on the hydrocarbon moiety;
   with the proviso that when 2 or more same or different bonds are inserted in a compound of (ii') or (iii'), the bonds are not adjacent.

10. The absorbent article according to claim 1, wherein the blood slipping agent is selected from the group consisting of following items (A)-(F), and any combination thereof:
   (A) an ester of (A1) a compound having a chain hydrocarbon moiety and 2-4 hydroxyl groups substituting for hydrogens on the chain hydrocarbon moiety, and (A2) a compound having a chain hydrocarbon moiety and 1 carboxyl group substituting for a hydrogen on the chain hydrocarbon moiety;
   (B) an ether of (B1) a compound having a chain hydrocarbon moiety and 2-4 hydroxyl groups substituting for hydrogens on the chain hydrocarbon moiety, and (B2) a compound having a chain hydrocarbon moiety and 1 hydroxyl group substituting for a hydrogen on the chain hydrocarbon moiety;
   (C) an ester of (C1) a carboxylic acid, hydroxy acid, alkoxy acid or oxoacid comprising a chain hydrocarbon moiety and 2-4 carboxyl groups substituting for hydrogens on the chain hydrocarbon moiety, and (C2) a compound having a chain hydrocarbon moiety and 1 hydroxyl group substituting for a hydrogen on the chain hydrocarbon moiety;
   (D) a compound having a chain hydrocarbon moiety and one bond selected from the group consisting of ether bonds (—O—), carbonyl bonds (—CO—), ester bonds (—COO—) and carbonate bonds (—OCOO—) inserted between a C—C single bond of the chain hydrocarbon moiety;
   (E) a polyoxy $C_3$-$C_6$ alkylene glycol, or alkyl ester or alkyl ether thereof; and
   (F) a chain hydrocarbon.

11. The absorbent article according to claim 1, wherein the blood slipping agent is selected from the group consisting of ($a_1$) an ester of a chain hydrocarbon tetraol and at least one fatty acid, ($a_2$) an ester of a chain hydrocarbon triol and at least one fatty acid, ($a_3$) an ester of a chain hydrocarbon diol and at least one fatty acid, ($b_1$) an ether of a chain hydrocarbon tetraol and at least one aliphatic monohydric alcohol, ($b_2$) an ether of a chain hydrocarbon triol and at least one aliphatic monohydric alcohol, ($b_3$) an ether of a chain hydrocarbon diol and at least one aliphatic monohydric alcohol, ($c_1$) an ester of a chain hydrocarbon tetracarboxylic acid, hydroxy acid, alkoxy acid or oxoacid with 4 carboxyl groups, and at least one aliphatic monohydric alcohol, ($c_2$) an ester of a chain hydrocarbon tricarboxylic acid, hydroxy acid, alkoxy acid or oxoacid with 3 carboxyl groups, and at least one aliphatic monohydric alcohol, ($c_3$) an ester of a chain hydrocarbon dicarboxylic acid, hydroxy acid, alkoxy acid or oxoacid with 2 carboxyl groups, and at least one aliphatic monohydric alcohol, ($d_1$) an ether of an aliphatic monohydric alcohol and an aliphatic monohydric alcohol, ($d_2$) a dialkyl ketone, ($d_3$) an ester of a fatty acid and an aliphatic monohydric alcohol, ($d_4$) a dialkyl carbonate, ($e_1$) a polyoxy $C_3$-$C_6$ alkylene glycol, ($e_2$) an ester of a polyoxy $C_3$-$C_6$ alkylene glycols and at least one fatty acid, ($e_3$) an ether of a polyoxy $C_3$-$C_6$ alkylene glycol and at least one aliphatic monohydric alcohol, and ($f_1$) a chain alkane, and any combination thereof.

12. The absorbent article according to claim 1, wherein in the excretory opening contact region, the blood slipping agent is attached to the surfaces of the fibers of the nonwoven fabric or woven fabric as droplets or particulates.

13. The absorbent article according to claim 1, wherein the top sheet has been subjected to hydrophilicizing treatment.

14. An absorbent article according to claim 1, wherein the absorbent article is a sanitary napkin or panty liner.

* * * * *